United States Patent
Lugtigheid et al.

[19]

[11] Patent Number: 6,158,434
[45] Date of Patent: Dec. 12, 2000

[54] VENTILATORY SYSTEM WITH ADDITIONAL GAS ADMINISTRATOR

[75] Inventors: Gerard Lugtigheid, Spijkenisse; Albert Grootendorst, Poortugaal, both of Netherlands

[73] Assignee: Henk W. Koster, Monte Carlo, Monaco

[21] Appl. No.: 09/125,851

[22] PCT Filed: Feb. 27, 1996

[86] PCT No.: PCT/EP96/00814

§ 371 Date: Nov. 13, 1998

§ 102(e) Date: Nov. 13, 1998

[87] PCT Pub. No.: WO97/31670

PCT Pub. Date: Sep. 4, 1997

[51] Int. Cl.[7] .................................................. A61M 16/00
[52] U.S. Cl. ................... 128/204.22; 128/205.24
[58] Field of Search ................ 128/204.18, 204.21, 128/204.22, 204.23, 205.24, 205.11

[56] References Cited

U.S. PATENT DOCUMENTS

| | | | |
|---|---|---|---|
| 3,727,627 | 4/1973 | Bird et al. | 137/100 |
| 4,256,100 | 3/1981 | Levy et al. | 128/204.21 |
| 4,345,612 | 8/1982 | Koni et al. | 128/204.21 |
| 4,579,568 | 4/1986 | Ricciardielli et al. | 155/189 |
| 4,686,974 | 8/1987 | Sato et al. | 128/204.23 |
| 4,829,183 | 5/1989 | McClatchie et al. | 250/346 |
| 5,048,515 | 9/1991 | Sanso | 128/204.26 |
| 5,209,761 | 5/1993 | Ivester et al. | 55/21 |
| 5,315,990 | 5/1994 | Mondry | 128/205.11 |
| 5,423,313 | 6/1995 | Olsson et al. | 128/204.21 |
| 5,471,977 | 12/1995 | Olsson et al. | 128/204.22 |
| 5,531,218 | 7/1996 | Krebs | 128/203.12 |
| 5,651,358 | 7/1997 | Briend et al. | 128/203.12 |
| 5,720,276 | 2/1998 | Kobatake et al. | 128/204.18 |
| 5,868,133 | 2/1999 | DeVries et al. | 128/204.21 |
| 5,871,009 | 2/1999 | Rydgren et al. | 128/204.18 |
| 5,909,731 | 6/1999 | O'Mahony et al. | 128/205.24 |
| 5,964,220 | 10/1999 | Boussignac et al. | 128/204.18 |

FOREIGN PATENT DOCUMENTS

| | | |
|---|---|---|
| 0 640 357 | 3/1995 | European Pat. Off. . |
| 43 12 431 | 4/1994 | Germany . |
| 2 016 279 | 9/1979 | United Kingdom . |
| 2 283 179 | 5/1995 | United Kingdom . |
| 84/02656 | 7/1984 | WIPO . |
| 91/14476 | 10/1991 | WIPO . |
| 95/10173 | 4/1995 | WIPO . |

OTHER PUBLICATIONS

"Tracheal Gas Insufflation during Pressure–Control Ventilation", Nahum A., et al., AM Rev Respir Dis, 1992; 146:1411–1418, Jul. 24, 1992.

*Primary Examiner*—Aaron J. Lewis
*Assistant Examiner*—Teena Mitchell
*Attorney, Agent, or Firm*—Heller Ehrman White & McAuliffe

[57] ABSTRACT

A ventilatory system for ventilating a patient includes a gas administration module for administering a predetermined amount of an additional gas, such as NO, to the patient, the gas administration module being provided with a predetermined number of parallel valve units each provided with a throttle valve and a controlled valve in series, the internal volume between the throttle valve and the controlled valve being so small that no interfering effects occur due to opening and closing of the controlled valve with a frequency below a maximum frequency. Preferably, the system is also provided with a tracheal gas insufflation (TGI) module and a measurement system for measuring the concentration of the additional gas.

25 Claims, 12 Drawing Sheets

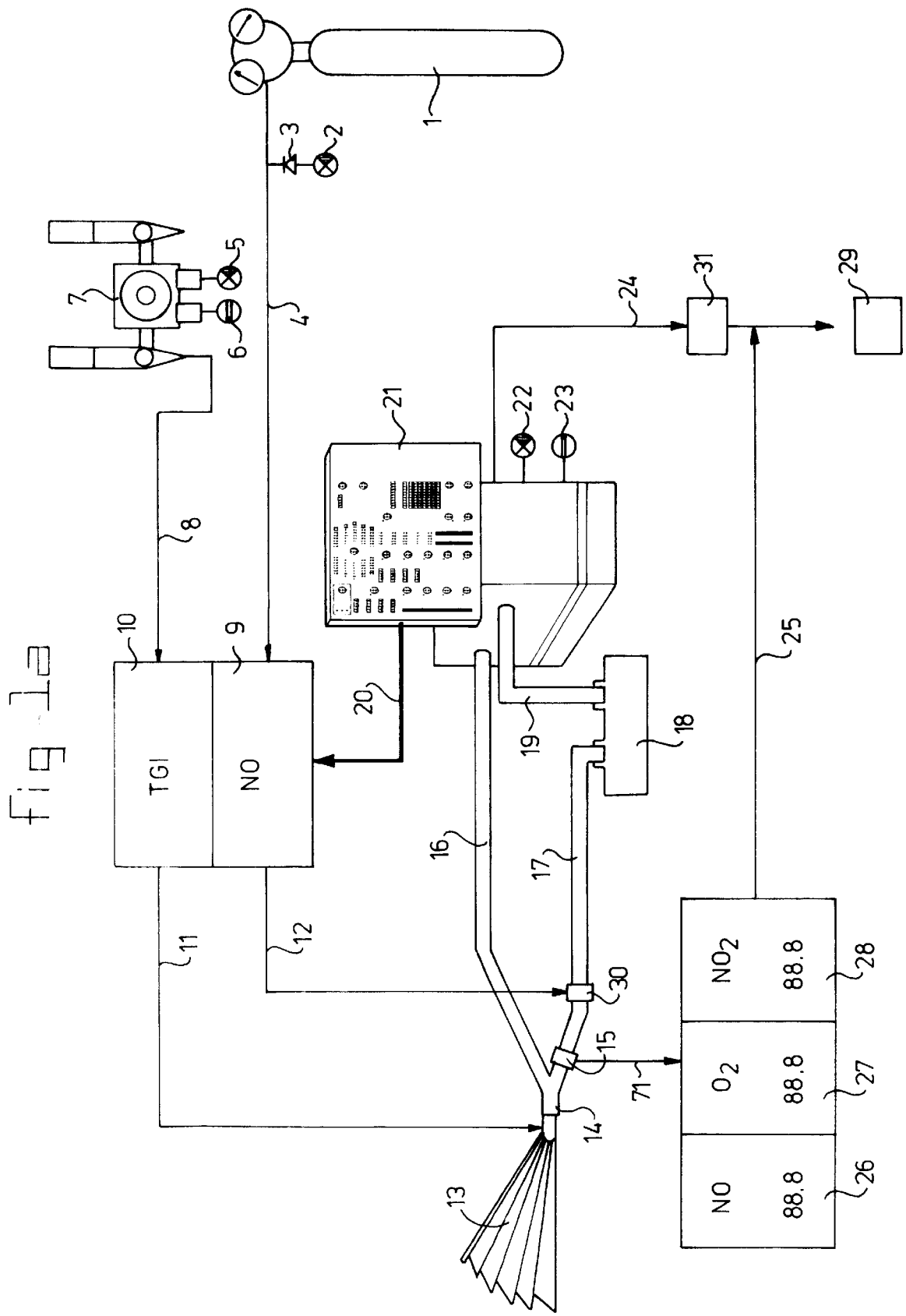

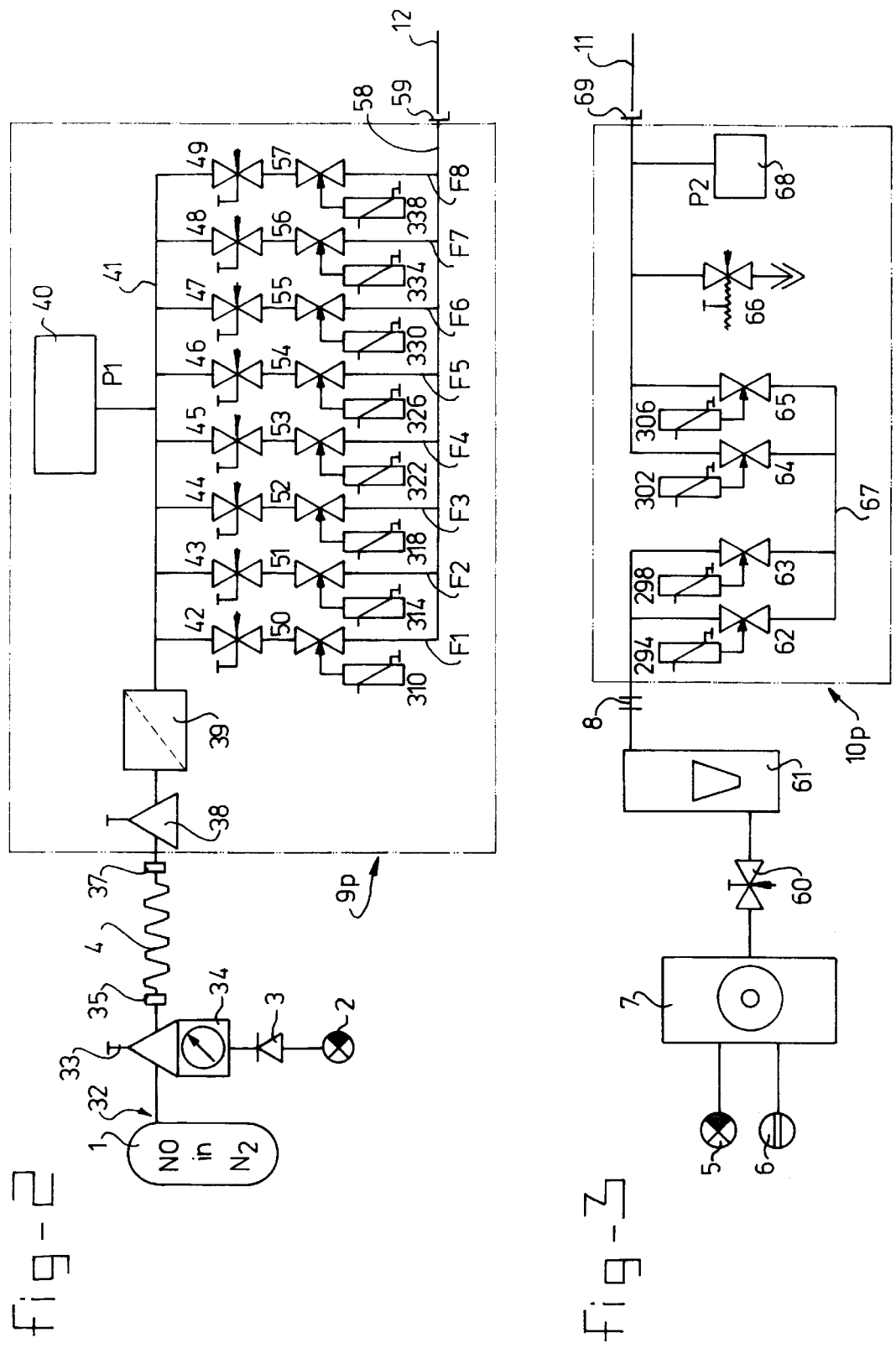

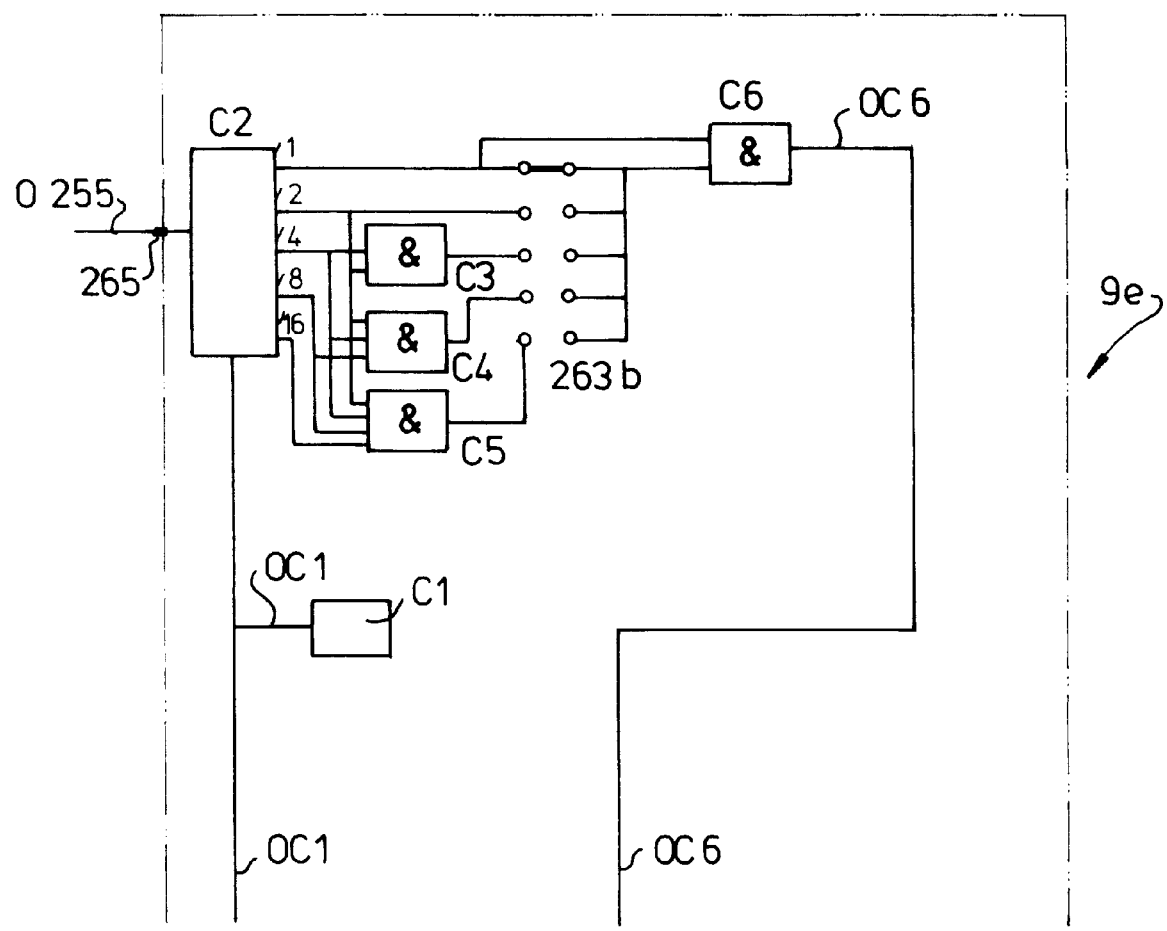

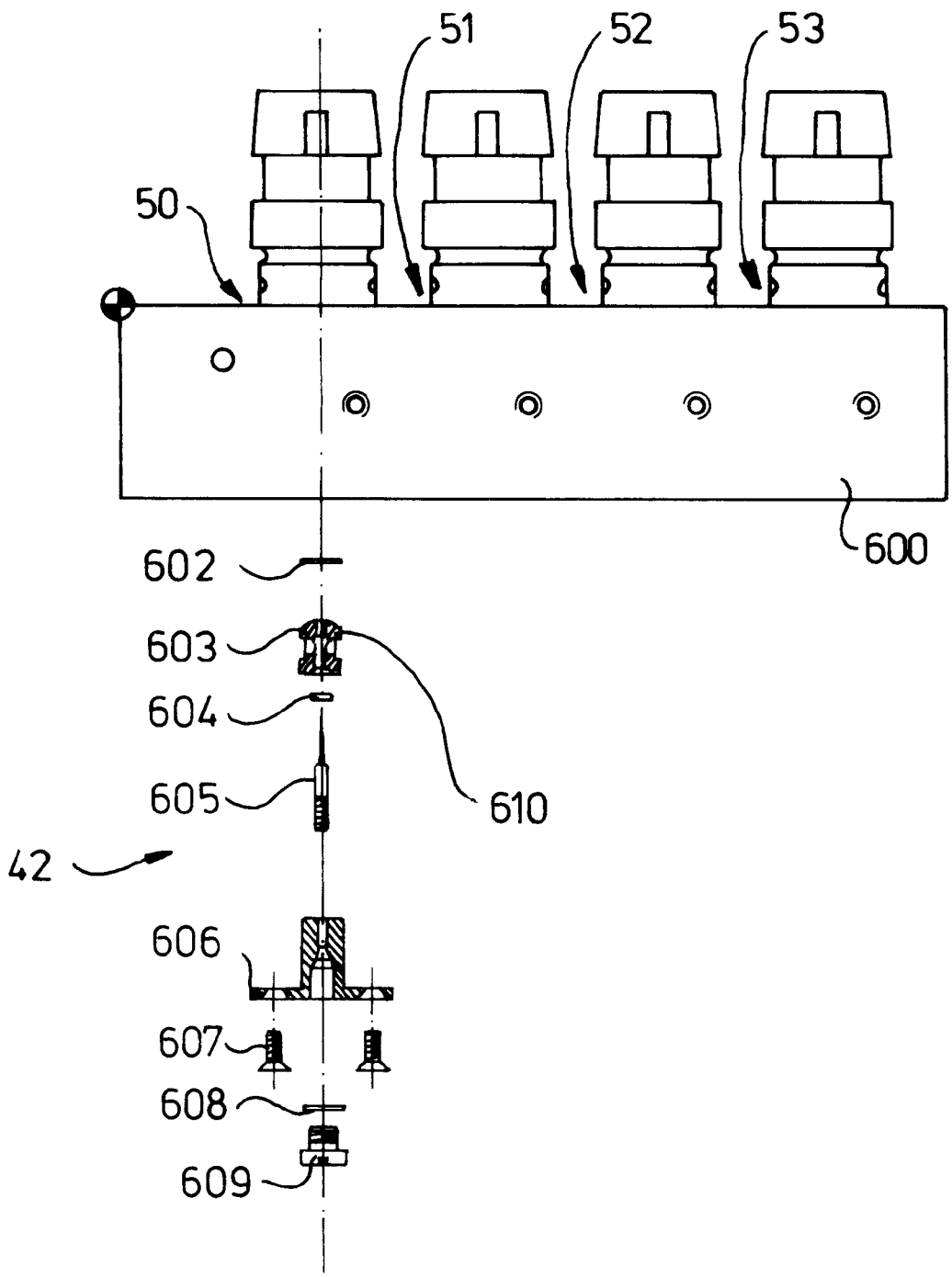

VENTILATORY SYSTEM WITH ADDITIONAL GAS ADMINISTRATOR

BACKGROUND OF THE INVENTION

1. Field of the Invention

This invention relates to a gas ventilatory system for ventilating a patient.

2. Description of Related Art

The present invention relates to a ventilatory system for ventilating a patient, comprising a ventilator provided with at least one first inlet for supplying a predetermined first gas mixture to the ventilator, at least one outlet for supplying a controlled amount of the predetermined first gas mixture to the patient during inspiration intervals, the ventilatory system furthermore having a gas administration module connected either downstream or upstream from the ventilator and arranged for administering a predetermined amount of an additional gas to the patient, the gas administration module being provided with a predetermined number of valve means which are connected in parallel and can each be independently switched between a closed state and an open state for supplying a predetermined amount of the additional gas to the patient, each of the valve means being provided with a series connection of a throttle valve with a throttle valve inlet and outlet and a controlled valve with a controlled valve inlet and outlet, the controlled valve being switchable between an open and closed state with a predetermined frequency, the throttle valve outlet being connected to the controlled valve inlet such that there is a passage with a volume V between the throttle valve and the controlled valve.

Such a system is known to the inventors from the firms Dräger and Nodomo.

GB-A-2,016,279 discloses a rate of flow controlled automatic medical breathing apparatus. The apparatus comprises a first controlled valve and a second controlled valve downstream from the first controlled valve. Between the first and second valves there is a lone for the flow of a predetermined gas. This line has a side connection to pressure regulating means which generate a control signal for the first valve when the pressure within the line exceeds a predetermined level such that the pressure within the line remains substantially constant.

U.S. Pat. No. 5,471,977 discloses an apparatus for the control of an extremely small additional gas flow to a respiratory gas flow. The apparatus is provided with valves and flow meters for the supply of air and oxygen, and an additional valve and flow meter for the supply of an additional amount of gas like $N_2$ and NO. The additional valve is controlled independently from the other valves.

The system according to the invention might be used for administering nitric oxide to a patient. Nitric oxide (NO) is a gas with potent vasodilatory properties. Recently, NO is found to have a beneficial effect on oxygen exchange in the lungs of patients with the adult respiratory distress syndrom (ARDS), a serious lung disease that, if untreated, leads to death due to lack of oxygen. ARDS may for instance occur after sepsis (i.e. bacteria or their products in the blood stream), multiple fractures or inhalation of toxic gases. All ARDS patients have to be artificially ventilated in the usual way. Administration of correctly measured NO to these ventilated patients would improve this treatment substantially. Several industrial prototypes have been developed. However, these prototypes suffer from serious problems. Factors causing these problems include:

1. NO reacts with oxygen and produces NO2 and other noxious NOx products. This NOx generation depends on oxygen concentration, time, pressure, temperature and relative humidity and occurs within seconds. NO is therefore stored in N2 usually in concentrations of 100 or 1000 ppm. Because most of the prototypes mix NO with oxygen upstream from the prototypes ventilator, the contact time is relatively long. The known downstream systems operate with more than one gascylinder, these gascylinders differ in NO concentration to cover the relevant clinical range.

2. The addition of NO to O2 decreases the amount of oxygen that can be delivered as large amounts of N2 are supplied together with the NO.

The first problem mentioned above would be solved by adding NO downstream from the ventilator, however, this is impossible with the present designs, without changing the gascylinder. The second problem mentioned above would require higher NO concentrations within the N2 of up to 5000 ppm, thereby improving the NO/N2 ratio. However, this would require greater precision of the NO administration system to a patient.

The ventilatory system according to the prior art lacks sufficient accuracy. The inventors of the present invention has found that this is due to the following problem. The NO module has several parallel valve means, each constituted by a series connection of a throttle valve and a controlled valve. Between the throttle valve and the controlled valve the NO passes through a passage with a relatively large volume. When the controlled valve is closed, still, some NO will flow into the passage thus increasing the pressure. If the controlled valve remains closed, the NO gas will flow through the throttle valve until the pressure within the passage equals the pressure of its inlet. However, when the passage is relatively large the time for neutralizing this interfering effect is relatively long. Actually, no standardization has taken place within the time period associated with the maximum operating frequency of the controlled valve. Thus, when the controlled valve opens again it may happen that the pressure within the passage is not well defined, resulting in an undefined amount of NO administration.

SUMMARY OF THE INVENTION

Therefore, a primary object of the present invention is to provide a ventilatory system which is provided with additional gas administration means which allow administration of a very accurate additional dosage of gas to the output of the ventilator to the patient.

A further object is to provide a ventilatory system arranged for administring a very accurate dosage of NO to the patient.

The primary object of the invention is obtained by a ventilatory system for ventilating patients as defined above which is characterized by the characterizing features of claim 1.

Any of the throttle valves may be constituted by a needle valve provided with an outlet element having an orifice, and an adjustable stem assembly for at least partly closing off the orifice. Such needle valves are very accurate, whereas the controlled valves may be simply used to either block or allow the flow through such a needle valve.

The volume referred to above is preferably less than 10 $mm^3$, even more preferably less than 3 $mm^3$. In the latter case no interfering effect was found at all up to an operating frequency of the controlled valves of 30 Hz.

Preferably, the operating frequency corresponds to switching the controlled valve at least 5 times every inspiration interval. Inspiration intervals may, e.g. last 0.1 to 2.0 sec.

Preferably, the valve means in their open states allow respective flow rates in accordance with a predetermined mathematical relation rising from a predetermined low value to a predetermined high value.

By using several valve means connected in parallel and having flow rates in accordance with such a predetermined mathematical relation rising from a predetermined low value to a predetermined high value very accurate control of the amount of added additional gas to the predetermined first gas mixture is obtained.

One possible mathematical relation would correspond to a binary flow bench. However, other mathematical relations can be selected.

The ventilatory system according to the invention is especially suitable for the administration of NO gas. NO may be added to the predetermined first gas mixture downstream from the ventilator. By adding the NO gas to the predetermined first gas mixture downstream from the ventilator a relatively short contact time between NO and oxygen is obtained, thus reducing the production of noxious NOx products.

Preferably, the flow rates are selected to allow administration of additional NO gas to the predetermined first gas mixture in a range of 0.05 to 100 ppm.

The ventilator of the system may be provided with an electrical output for providing control signals, the gas administration module being provided with electrical input means coupled to the ventilator's electrical output means for receiving the control signals in order to automatically control supplying the predetermined amount of the additional gas to the patient.

The electrical input means may be provided with a first input for receiving a flow control signal for controlling the amount of administered additional gas and a second input for receiving an inspiration control signal for controlling that the additional gas is administered during inspiration intervals of the patient.

The gas administration module may be provided with an electronic module which has a first amplifier connected to the first input and having a gain being switchable between a high and low value by means of a switch, the high and low values, respectively, corresponding to normal and high flow applications, respectively. The throttle valves can be adjusted for a neonatal or an adult application. The gain switch enlarges the application range.

In a further embodiment the electronic gas administration module may also be provided with a divider having a divider input connected to the second input for receiving the inspiration control signal and having a divider output for providing a divider output signal which corresponds to the inspiration control signal divided by a selectable dividing number, the divider output being connected to driving means of the valve means for controlling time sections during which the additional gas is administered. Thus, one is able to allow the administration of additional gas during preselected time sections in order to have a patient getting used to normal ventilation, i.e. without the administration of additional gas.

The administration system may be arranged such that also a small amount of additional gas is administered during expiration in the ventilatory system. Then, the electronic gas administration module is also provided with a third input for receiving an expiration control signal, for flow addition control and a fourth input receiving an expiration control signal from timing control.

By lack of the expiration timing control signal, the inversed inspiration timing control signal, the second input, can be used.

The expiration addition is determined by either the expiration flow signal which is connected to an input circuitry similar to the inspiration flow or a selectable value by means of jumpers. Corrections have been made for addition during normal and high flow application by means of switches and a second set of jumpers. When the inspiration divider is in use a blocking-circuitry prevents delivery during the non-delivery period.

The gas administration module may administer a predetermined amount of an additional gas to the patient, the gas administration module being provided with a predetermined number of valve means which are connected in parallel and can each be independently switched between a closed state and an open state for supplying a predetermined amount of the additional gas to the patient wherein each of the valve means is provided with a series connection of a throttle valve with a throttle valve inlet and outlet and a controlled valve with a controlled valve inlet and outlet, the controlled valve being switchable between an open aid closed state with a frequency lower than a predetermined maximum frequency, the throttle valve outlet being connected to the controlled valve inlet such that there is a passage with a volume V between the throttle valve and the controlled valve, the volume being less than 10 mm$^3$, preferably less than 3 mm$^3$.

Preferably, a tracheal gas insufflator module is added to the ventilatory system according to the invention. Understanding TGI requires some knowledge of artificial ventilation which is explained below. Artificial ventilation is a process by which a gas mixture is pushed into the lungs, usually via a tube that is introduced into the trachea of the patient. This tube is connected to an Y connector, one leg of which being connected to a valve that controls an expiration interval, whereas the other leg is connected to the ventilator which controls an inspiration interval and supplies the first predetermined gas mixture, mentioned above.

Inspiration is achieved by closing the expiration valve and opening the inspiration valve that separates the patient from the gas within the ventilator. Opening of the inspiration valve results in a gas flow from the ventilator to the patient until a preset volume or preset pressure is achieved. At that point the inspiration valve closes and after a predetermined time interval expiration is achieved by opening of the expiration valve.

In the lungs, oxygen is extracted from the inspiratory gas mixture and CO2 is added. CO2 removal is one of the important functions of artificial ventilation. A substantial volume in the lungs of the patient does not participate in gas exchange although it does communicate with the gas exchanging areas. This reservoir of dead space stores CO2 which decreases the gradient between blood CO2, alveolar CO2, ambient CO2 and therefore impairs CO2 removal.

By allowing a gas flow into the lungs after each end of an inspiration cycle and before the next inspiration cycle, the dead space CO2 can be washed out; such a flow should, however, stop immediately at the beginning of the next inspiration cycle. This requires a gas flow that starts immediately after closure of the inspiratory valve and stops at the opening of the inspiratory valve. The present invention is also directed to a TGI module that controls such a flow correctly.

Therefore, the system according to the present invention may include a tracheal gas insufflator (TGI) module provided with a pneumatic TGI module and an electronic TGI module, the pneumatic TGI module having a TGI inlet for receiving a predetermined second gas mixture and an TGI outlet for providing a predetermined amount of the second gas mixture, at least one controlled TGI valve connected between the TGI inlet and outlet and a pneumatic pressure limiting security valve connected downstream from the at least one controlled TGI valve, the electronic TGI module having electrical driving means connected to the at least one controlled TGI valve for controlling opening and closing of the at least one controlled TGI valve.

For safety purposes an adjustable pressure monitoring device may be applied which is able of blocking the TGI module in case of an increasing pressure.

Thus, simple means are provided for washing out CO2 from the dead space in the lungs of a patient. The pressure limiting valve ensures safety and a well defined output pressure. Although the principle of tracheal gas insufflation has been known before, no practical system for carrying out tracheal gas insufflation has been developed, as far as the inventors are aware of.

The at least one TGI valve means may comprise first TGI valve means connected to the TGI inlet means, the electrical driving means having first electrical-driving means connected to the first TGI valve means, the electronic TGI module and the first electrical driving means being arranged to open the first TGI valve means outside inspiration intervals.

In one embodiment, the first TGI valve means are provided with a first and a second controlled TGI valve in parallel.

Such a TGI module may be used in a ventilatory system defined above but can also be used in combination with other ventilatory systems known from the prior art.

One must consider that the application of a TGI module in combination with an NO module, the NO concentration is influenced by the flow from the TGI module.

Either the NO module must be capable of administering above 100 ppm or the TGI flow must have an addition of NO to the desired NO value.

Preferably, the pneumatic TGI module is connected at its inlet side to an air supply and an oxygen supply through a series connection of a blender, a needle valve and a flow meter. The flow meter is used to set the appropriate TGI flow to the patient. The blender is used to give the desired oxygen concentration to the patient.

The pneumatic TGI module may be provided with a pressure sensor to measure the pneumatic TGI module outlet pressure and to transmit a corresponding TGI outlet pressure signal to the electronic TGI module which is arranged to close the controlled TGI valve means whenever the TGI outlet pressure is not within a predetermined range.

Normally, when using a ventilatory system which is provided with an NO module for administering a predetermined amount of NO to a patient, the NO, NO2 and O2 concentrations are measured. The measured values are used to manually adjust the ventilator in order to supply the correct control signals. However, the functioning and response time of commercially available NO sensors and NO2 sensors are impaired by O2, pressure and water vapour that is always present in ventilatory circuits since, first of all, water vapour is always added to the inhalation to prevent airway siccation and, secondly, vapour is always present in exhaled gases anyway.

Therefore, it is a further object of the present invention to provide a measuring system, preferably in combination with the addition of a system as defined above, which is able to monitor the concentrations of NO, NO2 and O2 in the gas flows in the ventilatory system.

Therefore, the system according to the present invention may also include a measuring system comprising a measuring chamber, at least one gas component measuring sensor within the measuring chamber, a sample port for receiving gas samples, a water separator provided with a water separator inlet connected to the sample port, the water separator having a cooling unit for cooling the water separator to a dewpoint temperature between 0 and 10° C., preferably substantially 8° C., a first water separator outlet connected to water discharge means for draining separated water and a second water separator outlet connected to the measuring chamber for providing-dried gas samples.

An even better result will be obtained when the water separator is also provided with a predetermined volume of cooling liquid, e.g. water, which is cooled by the cooling unit, the water separator being arranged such that, in operation, the gas samples are led through the cooling liquid.

Preferably, the measuring system defined above is also provided with a cooling liquid level control unit for controlling the level of the cooling liquid within the water separator.

In a preferred embodiment, the measuring chamber of the measuring system comprises an NO sensor, an O2 sensor and pressure sensor and an NO2 sensor.

The measuring system defined above may be applied in the ventilatory system according to the invention but is also suited for use in other ventilatory systems.

BRIEF DESCRIPTION OF THE DRAWINGS

The present invention will be explained below with reference to several drawings which show one embodiment of the present invention but which are not intended to limit its scope.

FIG. 1a shows a general overview of a ventilatory system, partly in block diagram;

FIG. 2 schematically shows a pneumatic module of an NO module for administering NO to a patient;

FIG. 3 schematically shows a pneumatic module of a tracheal gas insufflation (TGI) module for washing out CO2 from the lungs of a patient;

FIG. 12a shows components of a specially designed valve for the present invention, partly in disassembled state;

DETAILED DESCRIPTION OF THE INVENTION

Figure 1B:
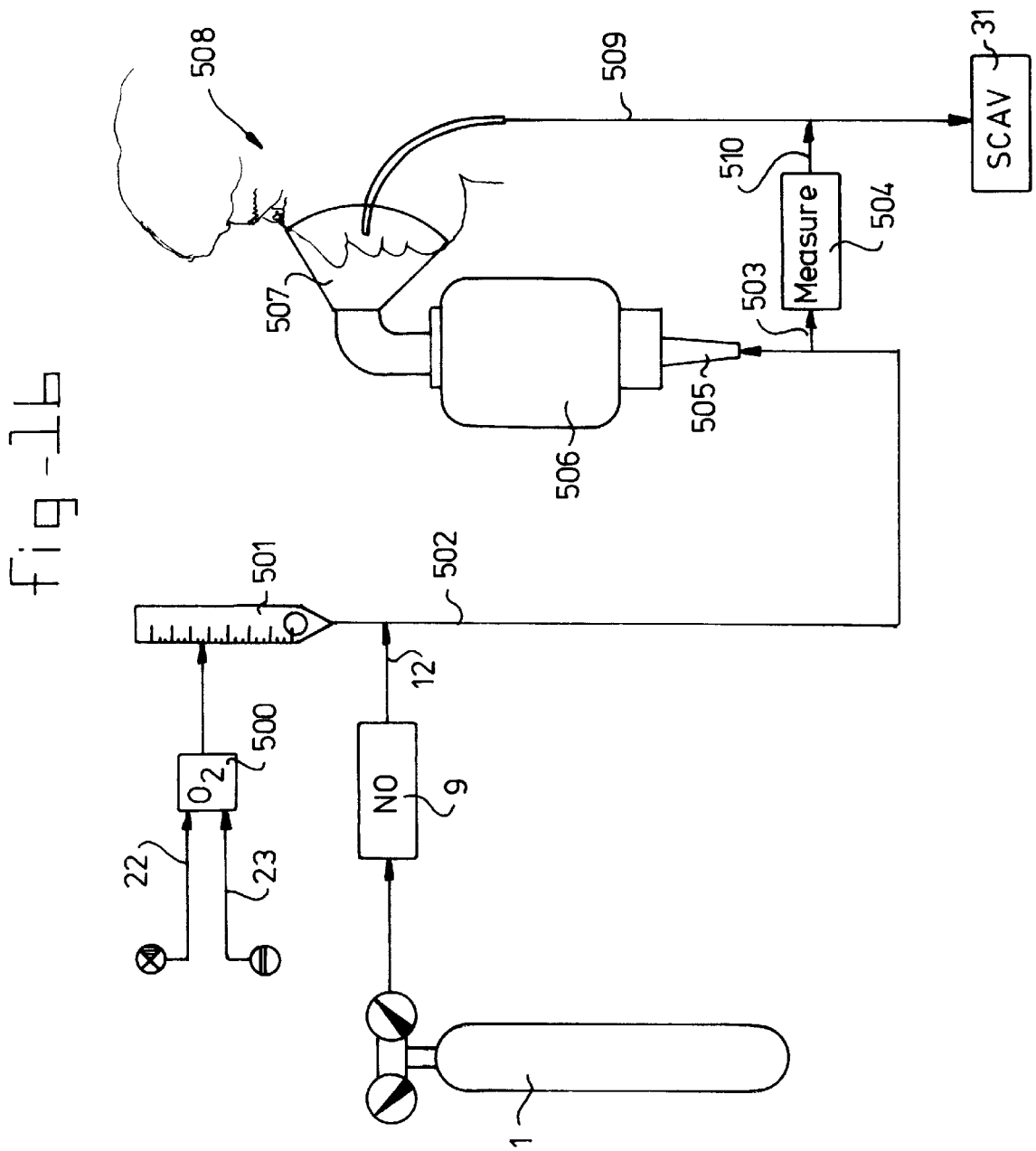
FIG. 1b shows an alternative ventilatory system, partly in block diagram, suitable for manual ventilation.

FIG. 1a shows an air ventilation system used to ventilate the patient by means of a ventilator 21 which is fed with air and oxygen. Air is available through an input 22 and oxygen is available through an input 23. The ventilator 21 may be of a commercially available type. The ventilator 21 outputs a mixture of air and oxygen towards the patient through a hose 19 which is connected to a humidifier 18. The humidifier 18 is connected to an Y connector 14 through a hose 17. The connector 14 is coupled to suitable means for supplying a mixture of air and oxygen to the lungs 13 of a patient.

Expiration gases from the lungs 13 flow backwards through the connector 14 and through a hose 16 to the ventilator 21. The ventilator 21 is connected to an output hose 24 which is connected either to a scavenging unit 31 or to a central evacuation system 29 available in any modern hospital. Ventilator 21 outputs the expiration gases through output hose 24.

The ventilator system shown comprises an NO module 9 and a tracheal gas insufflator (TGI) module 10. Both the NO module 9 and the TGI module 10 are provided with suitable pneumatics and electronics which will be explained in detail below.

The NO module 9 is connected to a gas bottle 1 through, preferably, a flexible pipe 4. The gas bottle 1 contains a high concentration of NO in N2. Such gas bottles are commercially available. It is to be understood that the present invention will be explained with reference to the administering of NO to a patient. However, the pneumatic and electronic circuitries shown can also be used for administering any other kind of gases to a patient.

Because of the high concentration of NO in the system a flush-out with air is provided through a non-return valve 3. The air is to be connected to an input 2.

The NO module 9 receives control data concerning timing and flow from the ventilator 21 through a cable 20.

The desired NO supply to the patient is delivered to the inspiration flow hose 17 through a suitable hose 12 which is connected to the hose 17 by means of a connector 30 within the hose 17, which connector 30 is, preferably, located approximately 20 cm upstream from the Y connector 14. The connector 30 and its distance from Y connector 14 depend on the size of the system applied, the ventilator type used, and the size of the patient. The optimum location of connector 30 can be determined experimentally. The mixing of NO from tube 12 and the gas flow from tube 17 also depends on the way NO is inserted. If it is inserted by connector 30 in a direction against the direction of flow in tube 17 the best mixing will result. Anyhow, the amount of NOx (x≧2) has to be kept to a minimum.

The ventilator 21 controls the NO module in order to supply NO to the inspiration flow through hose 17 in synchronism with the supplied air and oxygen.

Apart from the NO module 9 the system, preferably, comprises a TGI module 10. It is to be noted that the TGI module can also be applied separately in other ventilation systems.

The TGI module 10 is connected to a blender 7 which is connected to an air input 5 and an oxygen input 6. Moreover the blender 7 is connected to an accurate needle valve 60 and a flow meter 61 (see FIG. 3). The output of the flow meter 61 of the blender 7 is connected to the TGI module 10 by means of a suitable tube 8.

The TGI module 10 receives suitable control signals from the ventilator 21 through cable 20 and synchronizes gas delivery with expiration phases of ventilator cycles. The amount of gas delivered to the patient is set by flow meter 61 (FIG. 3) while the oxygen concentration is set by the blender 7. The gas mixture is administered into a tracheal tube placed in the patient's airway. This tube is provided with an additional lumen. These types of tubes are commercially available as tubes with a CO2 measuring lumen. The gas flow from the TGI module is administered through the common part of the Y connector 14 by means of a tube 11.

It is noted that the ventilator 21 must be able to receive a higher volume of gas from the patient than it has delivered through hose 19 since NO has been additionally delivered through connector 30 and TGI gas has been additionally delivered through tube 11.

The system shown in FIG. 1a also comprises an NO measuring device 26, an O2 measuring device 27 and an NO2 measuring device 28.

The measuring devices 26, 27, 28 receive a sample of the gas mixture. The sample is taken by means of a suction pump (not shown) through a sample port 15, which may be a 22 mm ISO conus with side connector which is commercially available. The sample port 15 may be located close to the Y connector 14 in the inspiration limb of the system. After measurement this sample flow can either be fed through an outlet tube 25 directly to the evacuation system 29. Alternatively, the sample taken can be fed through the outlet tube 25 to the scavenging system 31. As a further alternative, the sample may be fed back to the patient system by means of a sample port (not shown) in the system at the end of the expiration limb 16 adjacent the ventilator. This latter alternative is advantageous in neonatal applications.

The measuring devices 26, 27, 28 measure the NO gas, the O2 gas and NO2 gas, respectively, and monitor these gases on a minimal and maximal level.

This monitoring can be upgraded by measuring NO and NO2 in the expiration limb 16 by means of a sample port (not shown) just downstream of the Y connector 14.

Even more sophisticated monitoring can be achieved by measuring these gases by taking samples through a sampling port (not shown) in the Y connector 14. Then, both the inspired and the expired concentrations can be measured and the patients intake can be calculated from the difference of these concentrations. In this type of monitoring instantaneous measurement of NO is necessary.

Whereas FIG. 1a shows a ventilation system provided with a ventilator 21 which automatically controls the air supply, NO addition and TGI addition to a patient, FIG. 1b shows an alternative ventilation system which is manually controlled. In FIG. 1b reference numbers 1, 9, 12, 22, 23, and 31 refer to the same components as in FIG. 1a. Therefore, they will not be explained in detail again.

In the arrangement of FIG. 1b, a blender 500 receives air from air input 22 and oxygen from oxygen input 23. The output of blender 500 is connected to a flow meter 501 for setting the desired flow of the gas mixture of air and oxygen. Flow meter 501 is connected to an inlet 505 of a manual ventilation unit 506 through a hose 502. Output hose 12 of NO module 9 is connected to hose 502 by means of a suitable connector (not shown) to insert NO to the mixture of air and oxygen.

An inlet hose 503 of a measurement unit 504 is connected to the hose 502 by means of a suitable connector (not shown), preferably located near the junction of hose 502 and inlet 505. Measurement unit 504 is provided with an outlet hose 510 and with indicators (not shown) for indicating the NO concentration at inlet 505. In operation, measurement unit 504 takes samples of the gas mixture at inlet 505 and measures NO, O2 and NO2 contents.

The manual ventilation unit 506 is connected to a mask 507 which, in operation, is to be put over the mouth and nose of a patient 508. The mask 507 is provided with an output hose 509 leading to scavenging unit 31. Output 510 of measurement unit 504 is also connected to scavenging unit 31 by means of a suitable connector (not shown) in hose 509. Instead output hose 510 may have a direct connection to scavenging unit 31.

It is appreciated that the application of the mask 507 can be dispensed with. Instead of mask 507 means can be provided for a direct air supply into the trachea of a patient. Such means will avoid rebound effects when the ventilator itself is serviced.

In FIG. 2 a pneumatic NO module 9p which is part of the NO module 9, is shown. As stated above, the pneumatic NO module 9p may be used or adapted for other gases although, here, NO delivery will be described specifically.

Preferably, the gas bottle 1 is connected to a pressure regulator 33 by means of its main valve 32. The pressure regulator 33 is connected to a further pressure regulator 38 by means of, preferably stainless steel, flexible tube 4 which is provided with suitable connectors 35 and 37. Preferably, the outlet pressure of the pressure regulator 33 is at least $1,5.10^5$ Pa over the maximum setting of the further pressure regulator 38. The pressure regulator 33 is connected to the non-return valve 3. The inlet and outlet pressures of the pressure regulator 33 are, preferably, indicated by means of suitable manometers, generally indicated by reference number 34. Reference number 2 refers to the hospital's medical gas distribution system for providing air to the system.

Preferably, self-closing, quick-release couplers for NO and air should plug in and out with minimal loss of gas in order to maintain a safe level of NO in the working environment. Preferably, the NO connectors have a size different from the air connectors. A cross connection must be mechanically impossible.

The pressure regulator 38 is connected to a particle filter 39 to prevent dirt from entering a needle and valve system 42–57.

The outlet of filter 39 is connected to an inlet manifold 41 that feeds the needle and valve system 42–57. The pressure within manifold 41 is measured by a pressure transducer 40 which provides a pressure signal P1.

The needle and valve assembly comprises adjustable needle valves 42–49 mounted in parallel. In FIG. 2 eight needle valves are shown. However, it is understood that the number of valves 42–49 depends on the required accuracy as regards delivery concentration.

Any of the needle valves 42–49 is connected in series to one of a series of controlled valves 50–57, e.g. electromagnetic valves 50–57, respectively. Other types of controlled valves, e.g. pneumatically driven valves may be used instead. Each of the controlled valves 50–57 are normally closed and can be turned open by suitable drivers which are schematically depicted with references numbers 310, 314, 318, 322, 326, 330, 334 and 338, respectively, which will be explained below with reference to FIG. 5b. Each of the controlled valves 50–57 are connected to a main outlet manifold 58 which is connected to the tube 12 through a suitable, preferably self-locking, outlet connector 59.

Preferably, the amounts of flow F1 . . . F8 through the needle valves 42 . . . 49, respectively, when all controlled valves 50–57 are open, have a predetermined mathematical relation rising from a predetermined small value to a predetermined large value, or reverse. A very suitable mathematical relation is obtained when the system is built as a binary flow bench which means that:

$$F8=2.F7=4.F6=8.F5=16.F4=32.F3=64.F2=128.F1$$

However, any other suitable mathematical relation may be selected, if required.

In accordance with the present invention, special attention has been given to the design of the combination of any of the needle valves 42–49 and its corresponding downstream controlled valve 50–57. Accurate NO delivery requires a minimal enclosed compressible volume between the outlet of any of the needle valves 42–49 and the shut off of its corresponding controlled valve 50–57. Whenever any of the controlled valves closes the pressure in the enclosed compressible volume tends to rise until the pressure drop over the needle valve concerned is zero. However, some pressure increase will always occur leading to an unwanted reduction of accuracy of the dosage. For this reason, preferably, the needle valves 42–49 are positioned at the respective entries (seats) of the controlled valves 50–57 concerned.

The valve material is to be selected in accordance with the kind of gas to be delivered, i.e., chemical reactions must be prevented.

Figure 12B:
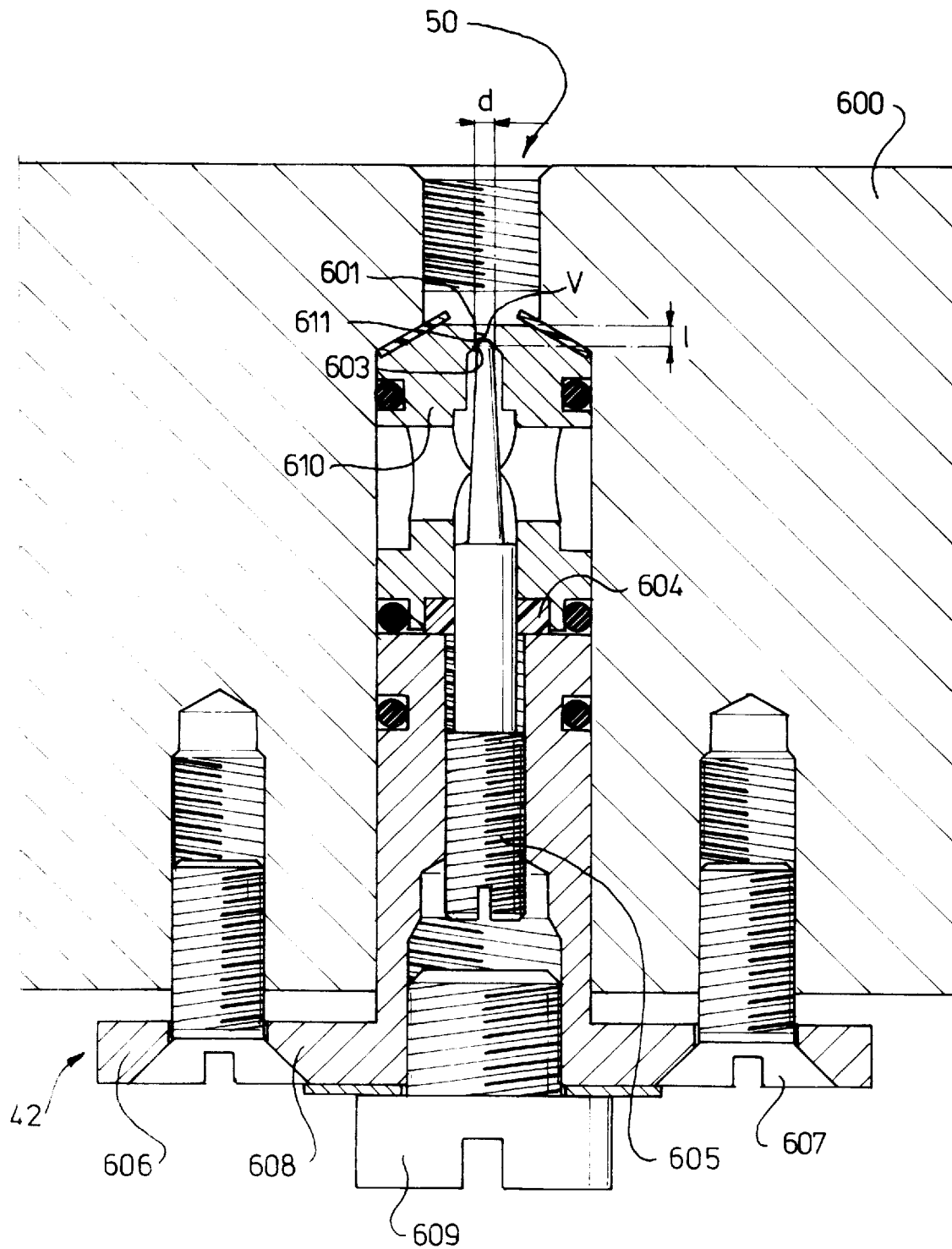
FIG. 12b shows the valve of FIG. 12a in its assembled state, partly in cross-section.

FIGS. 12a and 12b show one possible embodiment of such a needle valve in combination with a controlled valve. In FIG. 12a, reference number 600 refers to the body of the NO module 9. The body 600 is provided with controlled valves 50–57, four of which are shown. At the entry of these controlled valves 50–57 corresponding needle valves 42–49 are located, as stated above. FIG. 12a shows one of those needle valves 42 in its disassembled state. The needle valve 42 comprises a washer 602 and an outlet element 610. The outlet element 610 is provided with an orifice 603. Reference number 604 refers to a stem seal, whereas reference number 605 refers to a stem assembly. A slotted countersink head has been designated with reference number 606 which can be fixed to the body 600 with suitable bolts 607 or any other fixing means. Reference numbers 608 and 609, respectively, refer to a washer and a slotted head, respectively. The latter is provided for adjusting the stem assembly 605. The needle valve is preferably locked by locking means (not shown), e.g. by Locktite, after setting the desired flow. Locking by nail polish is also possible.

The valve housing 600 may be made of aluminum and consists of a system of channels. The parallel valves 50–57 are electronically controlled as will be described below. The regulation of the gas flow is based on the setting of the pressure regulator 38 (FIG. 2), the calibration of the needle regulator located on the valve seat and the timing of the valve's opening and shutting, as well as their number.

FIG. 12b shows the valves 42 and 50 (controlled valve 50 only being schematically indicated by its reference number since any type of controlled valve can be used here) in the assembled state. The same reference numbers refer to the same elements as in FIG. 12a.

As shown in FIG. 12b, outlet element 610 is 610 provided with orifice 603 which is to be partly closed by the needle tip of the stem assembly 605. Opposite to orifice 603 the outlet element 610 has an orifice 601 which is either closed or openened by controlled valve 50 (not shown in FIG. 12c). Between orifice 603 and orifice 601 outlet element 610 has a through hole 611 having a predetermined volume V. The through hole may have a cylindrical shape with a length l and a diameter d. Then, $V = l \times d^2 \pi / 4$.

A main requirement for the valves 42 and 50 in series is that at any time the controlled valve is opened a very accurately defined volume of NO is present in the enclosed volume V. A problem might be that when controlled valve 50 closes, still a very small portion gas flows through orifice 603 to the through 611 thus giving rise to a a pressure increase in the through hole. Of course, when it takes long for controlled valve 50 to open again, this pressure increase will have faded away by a return flow through orifice 603. However, when controlled valve 50 opens very fast the pressure in through hole 611 is not well defined, resulting in inaccurate NO supply. Therefore, the accuracy can only be guaranteed when the volume V of the through hole 611 is so small that the pressure within the through hole 611 has returned to the pressure at the inlet side of valve 42 at any time the controlled valve 50 opens. The inlet pressure of valve 42 is set by pressure regulator 38. For the addition of NO to air in ventilatory systems it has been found that the controlled valve 50 may advantageously be switched with a frequency of 30 Hz. Then, the internal volume of through hole 611 must be smaller than 10 mm$^3$, preferably smaller than 3 mm$^3$. In the latter case no interfering effects of through hole 611 were noticed. When the through hole 611 has a cylindrical shape it might, thus, have a length l=3 mm and a diameter d=1 mm.

It will be evident to persons skilled in the art that the exact volume of through hole 611 depends on the frequency of switching of controlled valve 50. The data given will also do for frequencies below 30 Hz.

The type of ventilator 21 and its volume in use and the required dosage range determine how the needles of the needle valves 42–49 should be calibrated. Some types of ventilators will provide more or less positive ventilation flow even during the expiration phase. Also the position of the NO inlet in the ventilation tubing system is important and user-dependent. Moreover, neonatal applications need a smaller dosage and a setting of the needle valves 42–49 to a lower flow. These parameters must be given in order to calibrate the needle valves 42–49 correctly for the required application.

A standard adjustments for a ventilator is:

Adults:
  Valve 57=60 ppm in 0.019 l/s
  Valve 56=60 ppm in 0.038 l/s
  Valve 55=60 ppm in 0.076 l/s
  Valve 54=60 ppm in 0.152 l/s
  Valve 53=60 ppm in 0.304 l/s
  Valve 52=60 ppm in 0.608 l/s
  Valve 51=60 ppm in 1.216 l/s
  Valve 50=60 ppm in 2.432 l/s Neonates:
  Valve 57=60 ppm in 0.0038 l/s
  Valve 56=60 ppm in 0.0075 l/s
  Valve 55=60 ppm in 0.0150 l/s
  Valve 54=60 ppm in 0.0300 l/s
  Valve 53=60 ppm in 0.0600 l/s
  Valve 52=60 ppm in 0.1200 l/s
  Valve 51=60 ppm in 0.2400 l/s
  Valve 50=60 ppm in 0.4800 l/s The difference between the neonatal and adult versions can be overcome by extending the number of valves.

It is appreciated that valves 50–57 are manually controlled in manual ventilatory systems as shown in FIG. 1b.

Now, a pneumatic TGI module 10p will be described with reference to FIG. 3.

It is noted that the TGI module 10 may be used with or without the NO module 9 and/or the measuring modules 26, 27, 28. The pneumatic TGI module 10p is connected to flow meter 61 by means of hose 8. This flow meter 61 is connected to the outlet of blender 7 through needle valve 60 which is provided with air inlet 5 and oxygen inlet 6, as explained above with reference to FIG. 1a. The flow meter 61 must be adjustable in the desired range and must be compensated for increased back pressure. Flow meter 61 may be either a manually or electrically adjustable flow meter. Preferably, all connections must be made to withstand pressures of up to $8.10^5$ Pa.

The pneumatic TGI module 10p comprises two parallel, normally closed controlled, e.g. electromagnetic, valves 62, 63 which are driven by suitable drivers, which are schematically indicated by reference number 294 and 298, respectively. The outlets of the valves 62, 63 are connected together to a TGI main manifold 67 which is also connected to inlets of parallel connected, normally closed controlled valves 64, 65. Controlled valves 64, 65 are driven by suitable drivers schematically indicated by reference numbers 302 and 306, respectively. The electronics to drive the controlled valves 62–65 will be described below with reference to FIG. 5a. Although two parallel valves 62, 63 in series with two parallel valves 64, 65 are shown any number of parallel or series valves may be realised. In the simplest embodiment only one controlled valve is provided.

Figure 5A:
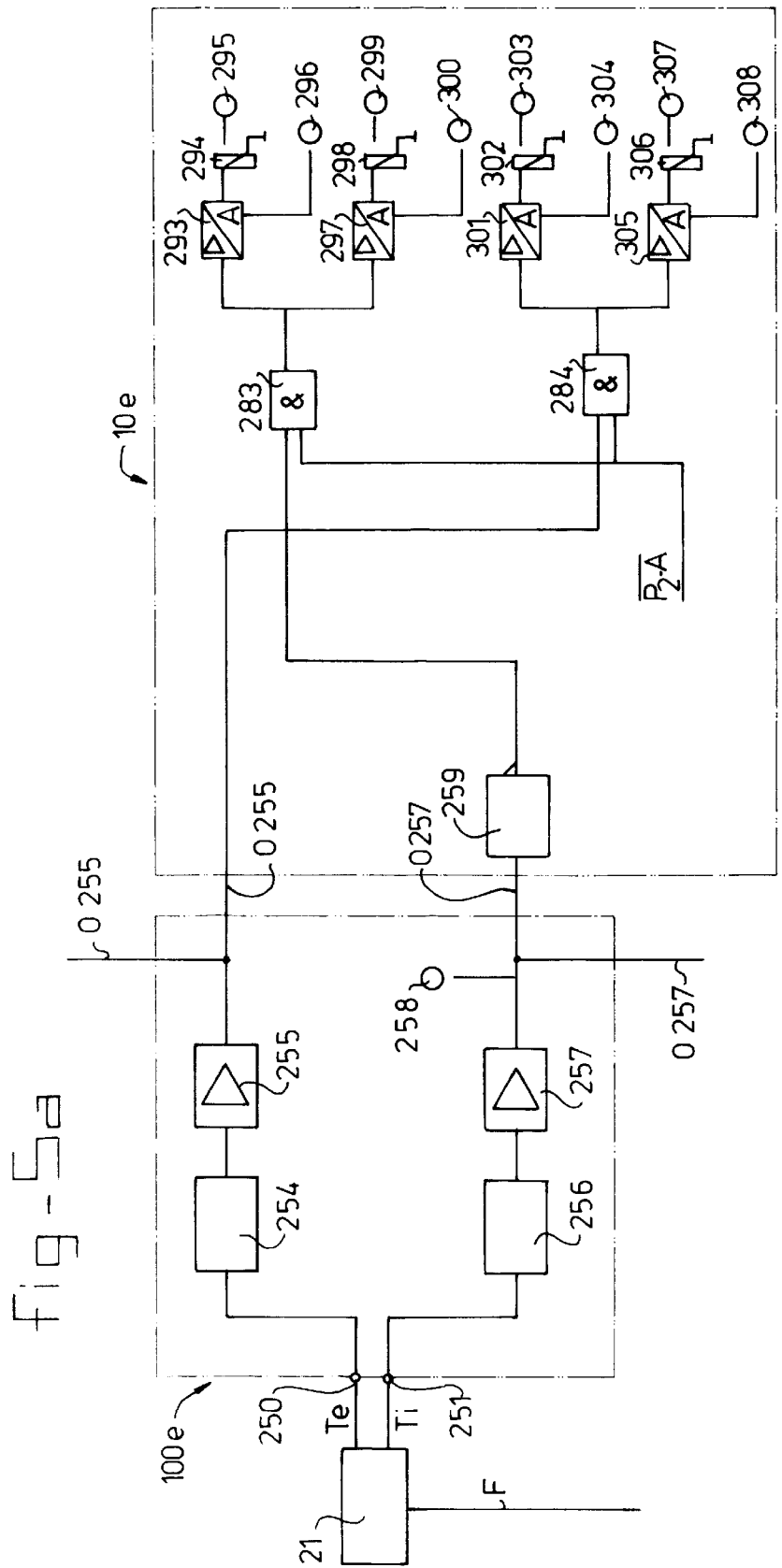
FIG. 5a shows, partly in block diagram, an electronic circuitry of the TGI module and of a control unit for supplying control signals to the electronic circuitry of the TGI module and to an electronic circuitry of the NO module, the electronic circuitry of the NO module being shown in FIGS. 5b and 5c.

The valves 62, 63 are switched by the inversed inspiratory flow phase. In other words, these valves 62, 63 are closed whenever there is a flow from the inspiration outlet of the ventilator 21. Controlled valves 64, 65 are switched by the expiration phase. There can be a significant and therapeutic time gap between the electric signals for controlling valves 62, 63 on the one side and valves 64, 65 on the other side. The switching signals must be synchronized in order that the TGI flow delivered by the pneumatic TGI module 10p occurs only once in each inspiration/expiration cycle. The purpose of providing valves 62, 63 controlled by the inversed inspiratory flow phase is to interrupt the TGI-module once a patient forces an unexpected inspiration when expiration is still expected and valves 64, 65 are kept open. During inspiration no TGI flow is allowed. The advantage of using both the inspiration timing signal Ti and the expiration timing signal Te (the signals are shown in FIG. 5a) is that the TGI module 10 may be applied with any type of commercially available ventilatory system which differ from one another in using both timing signals Ti, Te or only one of them. It is envisaged that instead of timing signals Ti, Te flow signal F is used since this latter signal also comprises information regarding inspiration and expiration phases and, thus, regarding the required timing of opening and closing the valves. This also holds for the NO module.

The TGI flow from the pneumatic TGI module 10p is delivered through tube 11 which is connected to both outlets of valves 64, 65 through a suitable connector 69. The pressure in the outlet line of the pneumatic TGI module 10p is measured by a pressure transducer 68. That pressure is indicated with reference number P2. Reference number 66 refers to a manually adjustable security valve connected to the outlet line of the pneumatic TGI module 10p to limit the pressure to a patient. In combination with at least one controlled valve 62, 63, 64, 65 the security valve 66 provides the TGI module lop with the possibility of a safe, controlled TGI flow.

Figure 4:
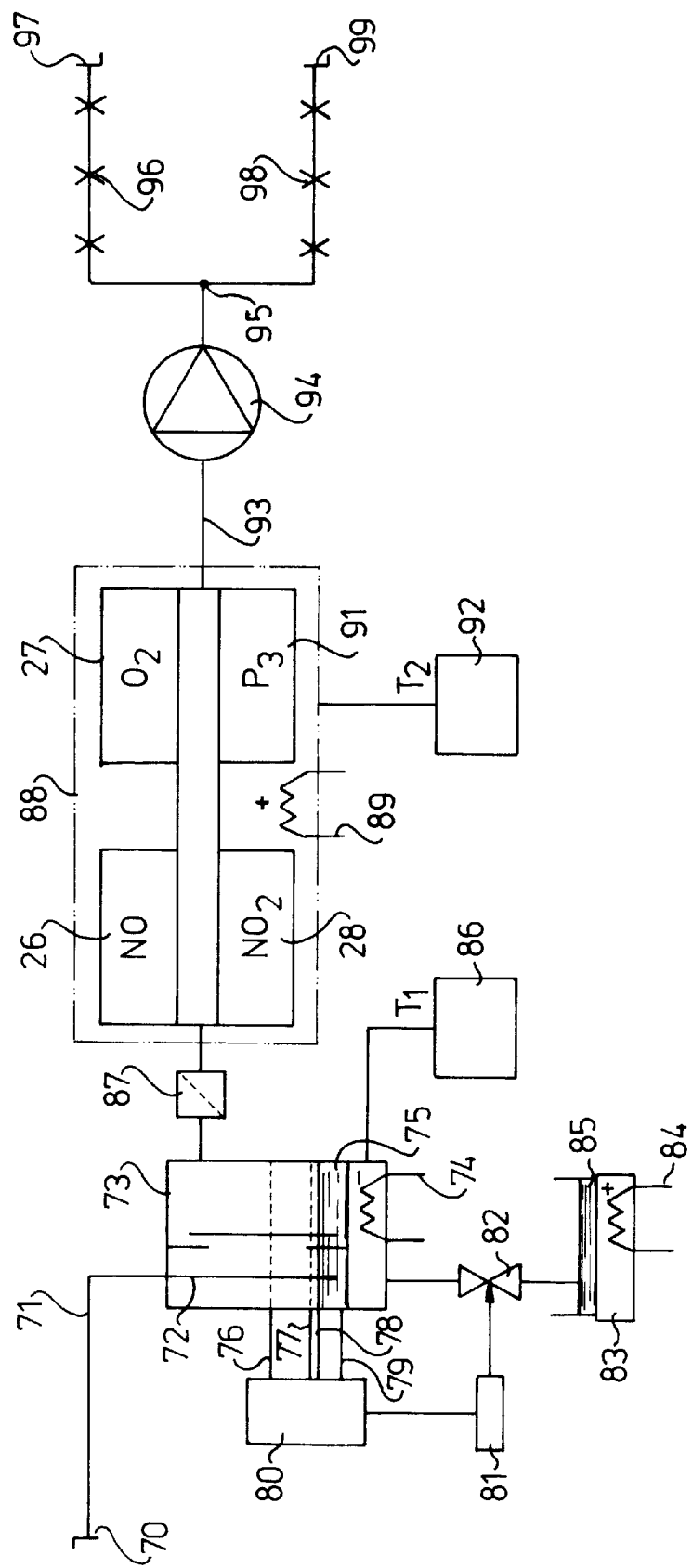
FIG. 4 schematically shows a measuring module for measuring NO, NO2 and O2.

FIG. 4 shows a pneumatic circuit for measuring NO concentration (26), O2 concentration (27), and NO2 concentration (28). The pneumatic circuit shown in FIG. 4 can be used in combination with the above circuits of FIGS. 2 and 3 or as a stand alone monitoring system for other types of gases or applications than the NO, NO2 and O2 applications described here.

The pneumatic circuit shown in FIG. 4 comprises a connector 70 connected to sample port 15 (FIG. 1a) and to a tube 71 which leads to a water separator 73. The tube 71 is connected to the tube 72 within the water separator 73. The water separator 73 comprises a Peltier element 74 for cooling the water separator to a temperature of a dewpoint of e.g. 8° C. in order to dry gas flowing through tube 71 towards a water separator 73. Preferably, the gas flow through tube 71 is led through a portion of cooled water 75 within the water separator 73. To this end, the internal tube 72 extends into the cooled water 75 such that the inflowing gas is pulled through the cooled water 75.

The temperature within the water separator 73 is controlled by a closed loop which will be explained below. The closed loop comprises a temperature sensor 86, e.g. a thermistor, which delivers a temperature signal T1 to a temperature control circuit shown in FIG. 10 which provides an appropriate input voltage to the Peltier element 74.

The level of the water 75 is controlled by means of two water level indicators: a maximum level indicator 77 and a minimum level indicator 78 which provide output signals to a driving circuit 80/81 for a controlled, e.g. electromagnetic, drain valve 82. The level indicators 77, 78 may be commercially available opto-elements. The driving circuit 80/81 controls the drain valve 82 in order to control the level of water 75 to be between the minimum and maximum levels monitored by indicators 77, 78. More details regarding a possible embodiment of driving circuit 80/81 for drain valve 82 are given below with reference to FIG. 6.

The outlet of drain valve 82 supplies drained water into either a removable container (not shown) or an open container 85 located on a support 83 which is provided with an adjustable heating element 84. Heating element 84 will be heated in operation to evaporate the collected water in the container 85 in the open air.

After being led through the water 75 the gas sample leaves the water separator 73 and enters a bacterial filter 87 to prevent contamination of a measuring chamber 88 which comprises the NO measuring module 26, the O2 measuring module 27 and the NO2 measuring module 28. The NO and NO2 measurements are influenced by the relative humidity of the gas entering the measuring chamber 88. By regulating the level of water 75 within the water separator 73 between the minimum and maximum levels indicated by indicator 77 and 78, the relative humidity of the gas inflow to the measuring chamber 88 can be correctly regulated.

For security reasons it is advisable to prevent inflow of moisture into the measuring chamber 88. Therefore, preferably, the measuring circuit according to FIG. 4 also comprises a level indicator 76 to indicate a high alarm level and a level indicator 79 to indicate a low alarm level. Like indicators 77, 78, the indicators 76 and 79 are also connected to the driving circuit 80/81 which controls the drain valve 82.

It is observed that the water separator 73 may be used in any ventilatory system where humidity in a gas or vapour has to be lowered.

Figure 11:
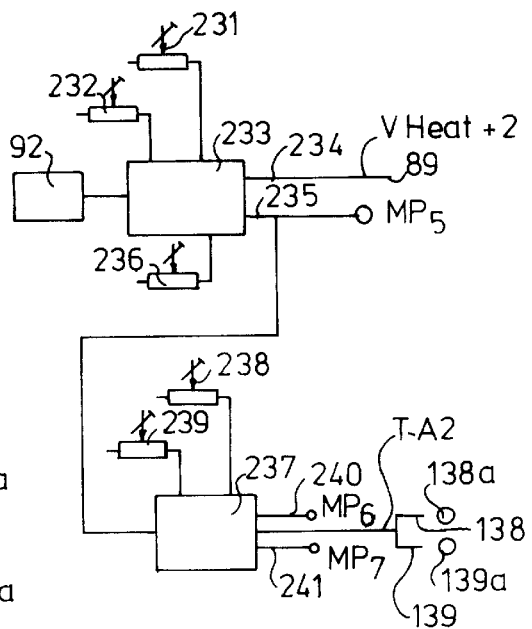
FIG. 11 shows a block diagram of a heating circuit.

The temperature within the measuring chamber 88 is measured by a temperature sensor 92, which delivers a temperature signal T2 to a temperature control circuit, an example of which is shown in FIG. 11. The control circuit shown in FIG. 11 provides a suitable control voltage to a heating element 89 within the measuring chamber 88 to keep the temperature in the measuring chamber 88 substantially constant to a set level.

Figure 8:
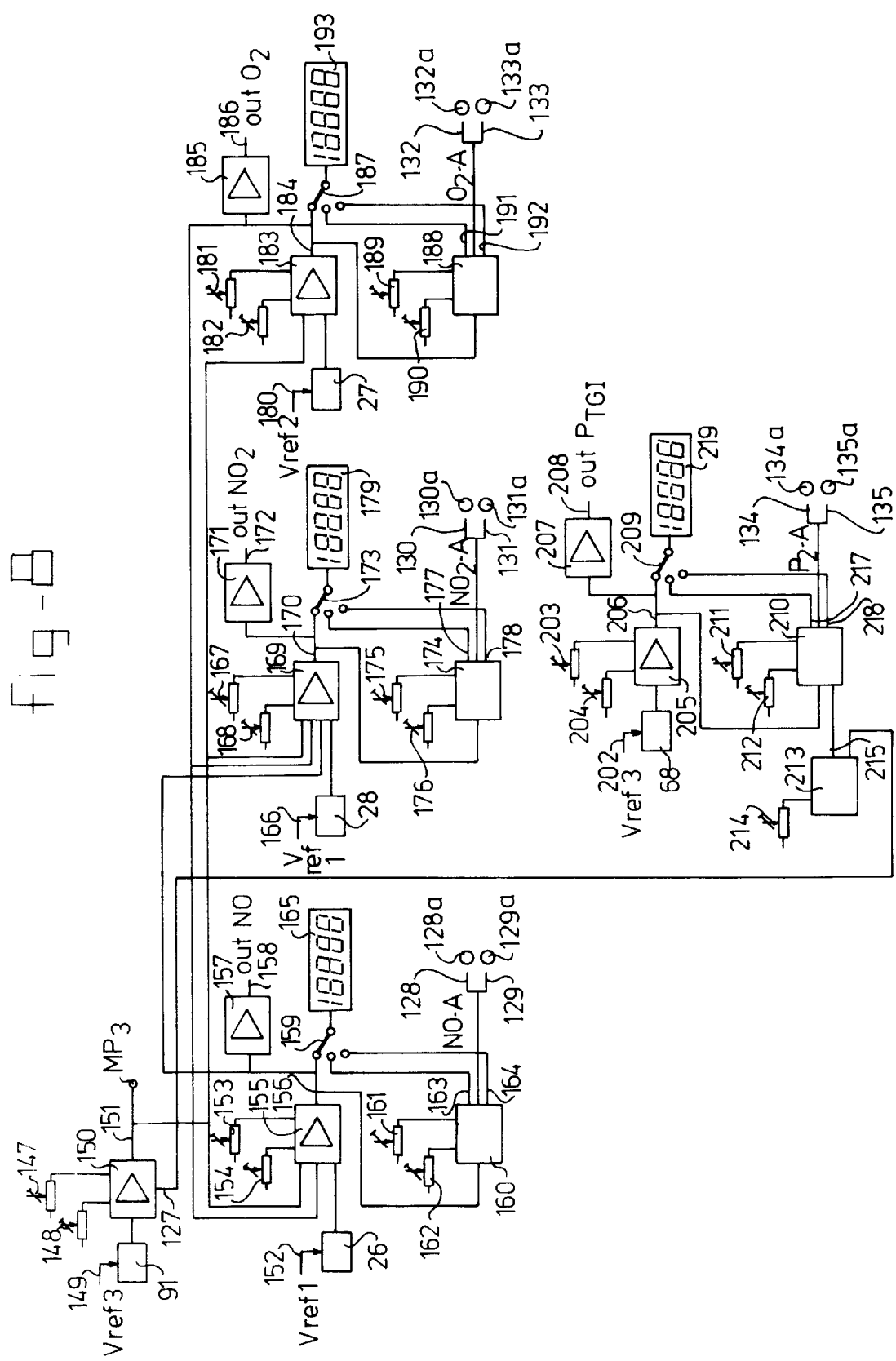
FIG. 8 shows a block diagram of a circuitry for measuring several pressures and gas concentrations occurring in the system according to the present invention.

The measuring chamber 88 comprises also a pressure sensor 91, which provides a pressure signal P3 to a measuring circuit shown in FIG. 8. This pressure signal is used to compensate the NO, NO2 and O2 for the increased pressure during artificial ventilation. The measuring chamber 88 is provided with an outlet 93 which is connected to a suction pump 94 which exhaust through a T-connector 95 to two capillary tubes 96, 98. One of the two capillary tubes, e.g. the one referred to with reference number 96, is suitable for use with adults, whereas the other, referred to with reference number 98, is suitable for neonate applications. Capillary tube 96 is connected to the evacuation system through a suitable connector 97, whereas the other capillary tube 98 may be connected to the evacuation system or ventilation system through a suitable connector 99. Note that only one of the connectors 97, 99 may be connected to the evacuation system at the same time, the other one is blocked.

The smaller the internal volume of the entire measurement circuit shown in FIG. 4, the better is the functioning of the measuring circuit since a small volume reduces mixing of a gas sample with older gas samples and reduces internal reactions.

Response time, sample flow and internal volume will be optimized in accordance with the required monitoring.

The amount of a sample flow taken at sample port 15 is determined by the size of the capillary tube 96 or 98, the choice is made based on the amount of the inspiration flow given by the ventilator 21 to the lungs 13 of the patient. The flow is related to the volume given to the patient which in turn is determined by the size of the patient. Adult sample flow outlet and neonatal sample flow outlet will be indicated separately.

Now, the electronic circuitries of the present invention will be described with reference to FIGS. 5a and 5b.

Figure 5B:
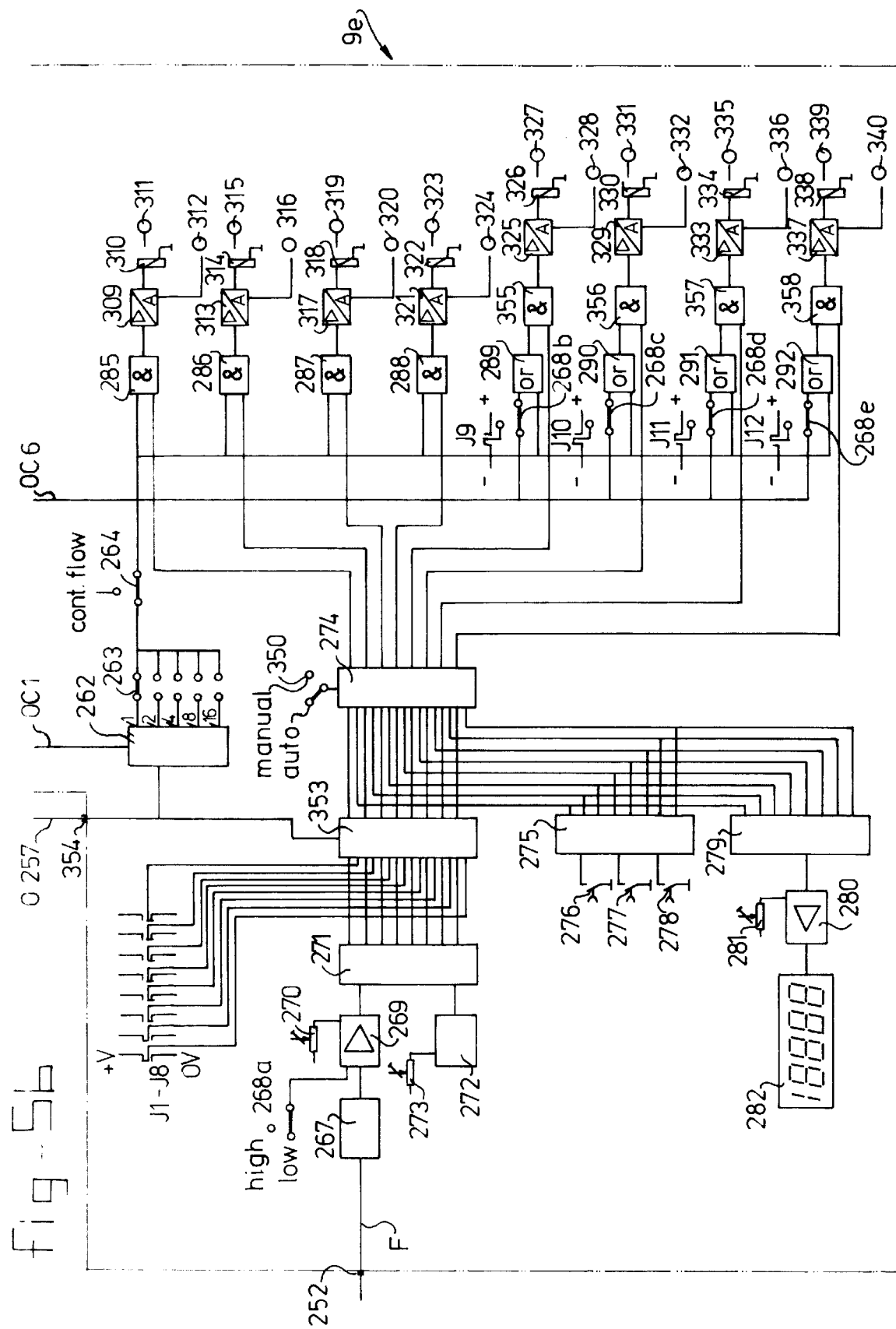

In FIG. 5a a common electronic control unit 100e and an electronic TGI module 10e are shown, whereas FIG. 5b shows an electronic NO module 9e. The common electronic control unit 100e provides control signals both to the electronic TGI module 10e and the electronic NO module 9e.

The control unit 10e receives an inspiration timing signal Ti through an input 251 and an expiration timing signal Te through input 250 from ventilator 21.

The inspiration timing signal Ti is supplied to a protector 256 which is connected to an amplifier 257 to be buffered and amplified in order, to keep the load on the ventilator 21 as low as possible. The protector 256 protects both the TGI module 10e and the NO module 9e against high voltages. The buffered inspiration timing signal Ti is indicated on an indicator 258 connected to the output of the amplifier 257.

The expiration timing signal Te is supplied to a protector 254, the output of which is connected to an amplifier 255 for amplifying and buffering the expiration timing signal Te. The protector 254 protects both the NO module 9e and the TGI module 10e against high voltages.

Amplifier 255 buffers and amplifies the expiration timing signal Te in order to keep the load on the ventilator 21 as low as possible. Amplifier 255 buffers an output signal 0255 both for the TGI module 10e and the NO module 9e. Amplifier 257 provides an output signal 0257 for both modules 9e and 10e.

The TGI module 10e comprises an inverter 259 which receives the output signal 0257 and transmits the converted signal to an input of an AND port 283. Another input of AND port 283 receives inverted alarm signal $\overline{P2\text{-}A}$ of a P2 measuring circuit, shown in FIG. 8. The output of the AND port 283 is connected both to an amplifier 293 and an amplifier 297. The outputs of the amplifiers 293 and 297 are connected to drivers 294 and 298, respectively, which drive controlled valves 62 and 63, respectively, as shown in FIG. 3. The status of the drivers 294 and 298 may be indicated by suitable indicators 295 and 299, respectively.

Amplifiers 293 and 297 buffer the signal from 283 to the electronic part of valve 294 and 298 of which operation is indicated by 295 and 299.

When the electronic part of the concerning valve or its amplifier disfunctions, the local alarm cicuitry routes an alarm to the central alarm unit 242 (FIG. 9) and indications 296 and 300.

The TGI module 10e also comprises an AND port 284 provided with two inputs. The first input of the AND port 284 is connected to the output of amplifier 255 and receives output signal 0255. The other input receives the inverted pressure alarm signal $\overline{\text{P2-A}}$. The output of the AND port 284 is connected to two amplifiers 301 and 305.

Amplifiers 301 and 305 buffer the signal from 284 to the electronic part of valve 302 and 306 of which operation is indicated by suitable indicators 303 and 307, respectively.

When the electronic part of the valve concerned or its amplifier disfunctions, the local alarm circuitry routes an alarm to the central alarm unit 242 (FIG. 9) and indicators 304 and 308.

The AND ports 283 and 284 receive inverted active pressure $\overline{\text{P2-A}}$ from the $P_2$ measuring circuit, as indicated in FIG. 8. which measures the pressure $P_2$ at the outlet of the pneumatic TGI module 10 (FIG. 3). The function is to block the TGI valves when the pressure on the module is too high. When no such inverted active pressure alarm signal $\overline{\text{P2-A}}$ is present the opening and closing of the controlled valves 62 and 63 is controlled by the inversed inspiration timing signal Ti whereas the controlled valves 64 and 65 are controlled by the expiration timing signal Te. Normally, the inspiration timing signal Ti is low when the expiration timing signal Te is high. However, when a patient forces an inspiration when Te is still high, Ti will be directly switched to a high state, thus, ensuring blocking valves 62, 63 and preventing any further TGI gas flow which is not allowed during inspiration phases. Thus, a safety measure is provided.

The electronic NO module 9e is shown in FIGS. 5b and 5c and is provided with three inputs 252, 354 and 265. Input 252 receives a flow signal F from the ventilator 21. Input 354 receives output signal 0257 from the control unit 100e and input 265 receives output signal 0255 from control unit 100e.

Output signal 0255 is supplied to a divider C2, able to divide its input signal by, e.g., 1, 2, 4, 8 and 16. The divider C2 outputs divided by 2 and 4 are connected to AND ports C3, C4 and C5. The divider output divided by 8 is connected to the AND ports C4 and C5, whereas the divider output divided by 16 is connected to AND port C5. The divider output divided by 1 is connected to an AND port C6, directly and through a switch 263b. The outputs of AND ports C3, C4 and C5 are connected to AND port C6 through switch 263b. The output of AND port C6 provides an output signal OC6.

An autosynchroniser C1 provides a synchronisation signal OC1 to divider C2.

The electronic NO module 9e comprises a divider 262 the input of which is connected to input 354. The divider 262 provides an output signal either during each inspiration phase or second, fourth, eighth or sixteenth inspiration phase. These division factors are examples and may be substituted by others. The dividing factor may be manually selected by a switch 263. The reason for providing the divider 262 is to provide the possibility of reducing the NO supply to a patient gradually in order to have the patient used to a normal air inspiration and expiration, ending his treatment in the hospital.

Divider 262 receives synchronisation signal OC1 from autosynchroniser C1 in order to be synchronised with divider C2.

In order to make the NO compensation during expiration only in the active period the expiration of every breath must be active by a division by one, and every first expiration stroke by dividing by two, every third expiration stroke by dividing by four. every seventh expiration stroke by dividing by eight, every fifteenth expiration stroke by dividing by sixteen. This is accomplished by AND ports C3, C4, C5 and C6. Switch 263b is coupled to switch 263.

The output of the divider 262 is connected to a two-state switch 264. In the first state connector 264 is connected to the output of the divider 262 whereas in the second state of switch 264 where it receives a predetermined voltage, the system operates then as a constant flow system, which is useful for manual ventilation. The output of switch 264 is connected to inputs of AND ports 285–288 and to inputs of OR ports 289–292. The outputs of AND ports 285–288 are connected to respective amplifiers 309, 313, 317 and 321. The amplifiers 309, 313, 317 and 321 provide suitable output signal to drivers 310, 314, 318, and 322, respectively, which drive controlled valves 50, 51, 52, and 53, respectively (see FIG. 2). Amplifiers 309, 313, 317 and 321 buffer the signal from AND ports 285, 286, 287 and 288 to the electronic part of valves 310, 314, 318 and 322, of which operation is indicated by 311, 315, 319 and 323.

When the electronic part of the valve concerned or its amplifier disfunctions, the local alarm circuitry routes an alarm to the central alarm unit 242 (FIG. 9) and indicators 312, 316, 320 and 324.

Amplifiers 325, 329, 333 and 337 buffer the signal from OR ports 289, 290, 291 and 292 to the electronic part of valves 326, 330, 334 and 338, of which operation is indicated by 327, 331, 335 and 339.

When the electronic part of the valve concerned or its amplifier disfunctions, the local alarm circuitry routes an alarm to the central alarm unit 242 (FIG. 9) and indicators 328, 332, 336 and 340.

As indicated in FIG. 5b the output signal OC6 of AND port C6 is supplied to OR ports 289–292 through switches 268b, 268c, 268d and 268e, respectively. These switches 268b–268e can be concurrently switched to the input 265 or to respective jumpers J9, J10, J11 and J12, respectively. The jumpers may be manually set to either a high (+) voltage or a low (−) voltage. In FIG. 5b jumper J9 and J10 are set to a low voltage and jumpers J11 and J12 to a high voltage. Thus, during expiration intervals, i.e. 0255=high and 0257= low, drivers 334 and 338 will be active to open valves 56 and 57. This compensates higher supply pressures, as will be explained below.

Through input 252 the electronic NO module 9e receives a flow signal F from the ventilator 21. The flow signal F is led to a protector 267, the output of which is connected to an amplifier 269. The amplifier 269 may be calibrated with suitable calibrating means 270. The amplifier 269 amplifies and buffers the flow signal F in order to keep the load on the ventilator 21 as low as possible. The amplifier 269 is provided with a further input which is connected to a switch 268a which connects said further input of the amplifier 269 either to a low voltage resulting in a low gain or to a high voltage resulting in a high gain. The switch 268a is used in either a normal or a high flow application which requires different flow ranges but can differ within those ranges substantially. Consequently, the application of more valves may be necessary. However, a gain adaption by means of switch 268a has been applied instead. The pressure needed to obtain the same amount of additive will be higher for a lower gain. If during expiration at a higher pressure the same number of valves should be opened the additive concentration is raised. For that reason, the components J9–J12 and 268b–268e are provided to allow selection of the number of valves to be used in high gain applications. Alternatively, the switch 268a may be omitted if the number of mechanical valves 42–49 is increased, thus, providing for more possible flow levels within a predetermined range.

Switch 268a is concurrently swichtable with switches 268b–268e. When switch 268a connects amplifier 269 to a high gain, then the OR ports 289–292 are connected to the jumpers J9–J12, respectively. When switch 268a connects amplifier 269 to a low gain, then the OR ports 289–292 are connected to the signal OC6 which is derived from the expiration timing signal Te. Thus, in the latter case, valves 54–57 remain open during expiration intervals, whereas valves 50–53 will be closed. However, when amplifier 269 is connected to its high gain input only valves 56 and 57 will be open during expiration intervals since only jumpers J11 and J12 are in a high voltage state. Thus, a compensation for the high gain state during expiration intervals is achieved. It is to be understood that FIG. 5b shows that four valves, i.e. 54–57, are also controlled by the expiration signal Te. However, this number may be more or less, as required.

The amplifier 269 provides an analog output signal to an analog to digital (A/D) convertor 271. The amplifier 269 is, for example, calibrated such that the gas delivery to a patient is 30 ppm where the needle valves are calibrated for a constant volume ventilation, a tidal gas volume of 600 ml, at 12 breaths per minute, with 25% of actual inspiration flow and a pressure on the needle valves of $10^5$ Pa. The A/D convertor 271 may be provided with 8 bits. The number of bits is the same as the number of valves 50–57. The convertion speed of the convertor 271 may be set by timing adjustment means 273 through a timing circuit 272 the output of which is connected to a suitable input of A/D convertor 271. The convertion speed may not exceed the maximum valve speed, i.e. the speed needed for a valve to switch between the closed and open state or reverse, and, preferably, corresponds to at least ten signals during each actual inspiration period.

The output of each of the bits of the A/D convertor 271 is connected to a corresponding input of a multiplexer 353. The multiplexer 353 is also provided with additional inputs connected to respective jumpers J1–J8 that may set to either a low voltage or a high voltage. The multiplexer 353 has an input connected to input 354 and thus receives input signal 0257. Multiplexer 353 is, thus, only active when the input signal 0257 is active, i.e. during an inspiration interval. Then, the multiplexer 353 carries the inspiration flow signal. During the expiration phase the multiplexer carries the selected voltages from the jumpers J1–J8. This creates the possibility of using the controlled valves 50–57 to administer some NO into the gas flow during expiration, for use with ventilators that are provided with that feature. Multiplexer 353 is provided with as many outputs as the number of outputs of A/D convertor 271. Each of the outputs of multiplexer 353 is connected to a respective input of a further multiplexer 274.

The multiplexer 274 is also connected to a preset counter 275 which can be manually counted down by means of switch 276 or up by means of a switch 277. Reset of counter 275 may be automatic on the start-up or manual by means of a switch 278. The output of the counter 275 is not only fed to the multiplexer 274 but also to a digital to analog (D/A) convertor 279. The output of the D/A convertor 279 is connected to an amplifier 280 which may be calibrated by suitable calibrating means 281. Calibration will be done in accordance with the required concentration of additive which is displayed on a display 282 connected to the output of amplifier 280. A switch 350 is connected to the multiplexer 274 in order to select which input signal is switched by multiplexer 274 to its output. If switch 350 is set in the manual mode the multiplexer 274 transmits the output signal of the counter 275 by means of which a fixed admixture is selected (constant flow). In the automatic mode the multiplexer 274 transmits the output signal of multiplexer 353 by means of which the admixture depends on the flow signal F from the ventilator 21.

The selected output signal of multiplexer 274 is sent to inputs of AND ports 285–288, and 355–358.

Thus, normally, the electronic NO module 9e controls the closing and opening of controlled valves 50–57 (see FIG. 2) by means of the input flow signal F present on input 252, input signal 0257 which is derived from the inspiration timing signal Ti and input signal 0255 which is derived from the expiration signal Te.

The electronic measurement, heating, cooling, power, and alarm circuits are shown in FIGS. 6–11.

Figure 6:
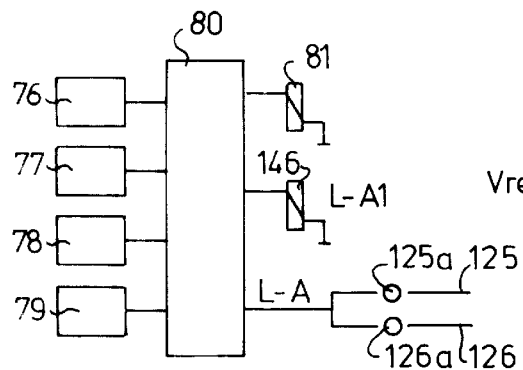
FIG. 6 shows a block diagram of a level detector to be used in a water separator used in the present invention.

FIG. 6 shows an electronic circuit for controlling the level of water 75 in the water evaporator 73 (FIG. 4). The circuit shown is provided with electronics 80 able to receive signals from the level indicators 76–79 and to provide output signals to the driving circuit 81 for the drain valve 82 and to a driving circuit 146 which will interrupt the sample pump 94 (FIG. 4) whenever the level indicator 76 indicates a situation of a high alarm level (see also FIG. 9). Then, also an alarm signal on a line 125 will be present which is indicated by an alarm indicator 125a.

Figure 9:
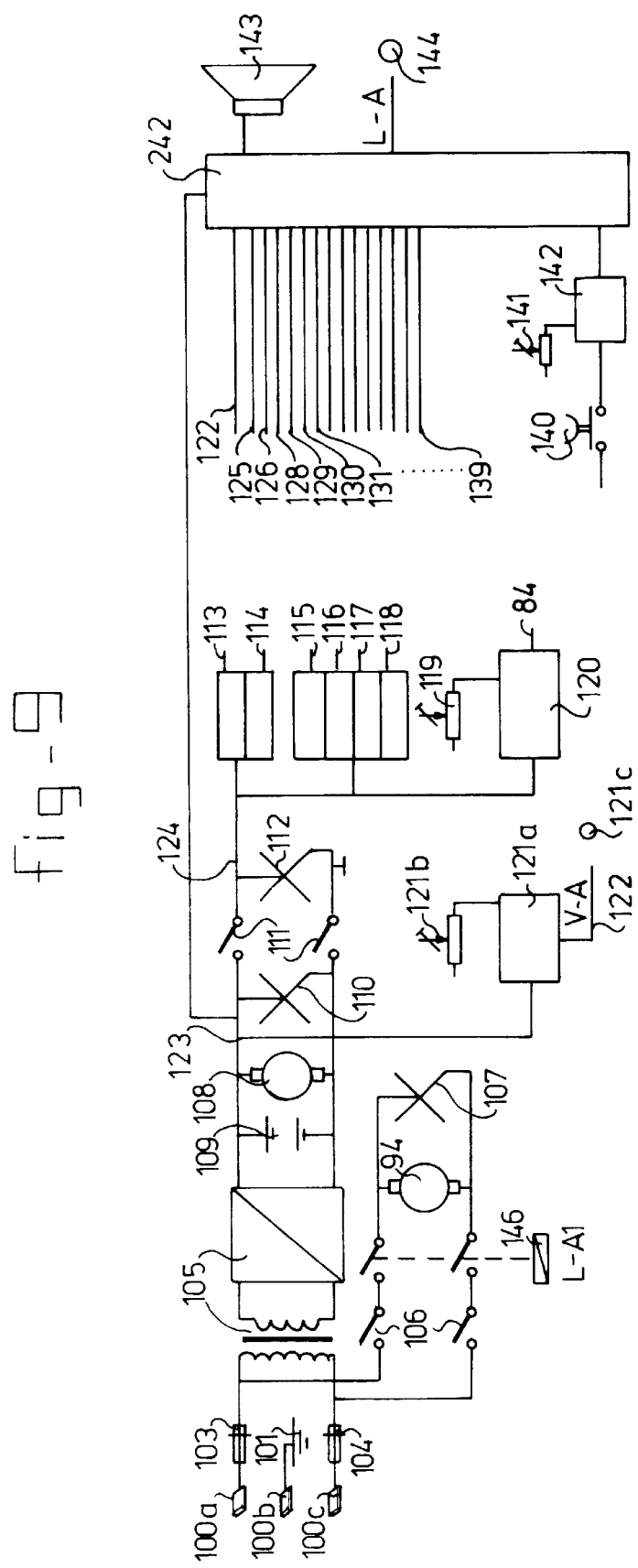
FIG. 9 shows a block diagram of a power unit, a heating unit and an alarm unit used in the system according to the present invention.

When level indicator 79 detects a situation of a low alarm level an alarm signal will be present on a line 126 which is indicated on an alarm indicator 126a. The indicators 125a and 126a may be of a different colour. Electronics 80 may consist mainly of level switches and drivers known to persons skilled in the art which need no further explanation. Alarms are fed to the central alarm unit 242 (FIG. 9).

Each of the sensors 26, 27, 28 in the measuring chamber 88 are influenced by pressure P3. As this pressure P3 varies for every situation the system is designed to compensate for these variations by means of a mean pressure value, obtained by integration. The pressure 93 is measured by pressure transducer 91 and averaged over an adjustable period of time but minimum one breathing ventilation cycle.

Figure 7:
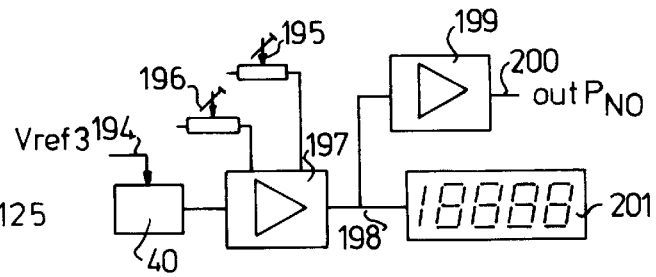
FIG. 7 shows a block diagram of a pressure measurement circuit.

The pressure P1 in the inlet manifold 41 of the pneumatic NO circuit shown in FIG. 2 is measured by transducer 40 which may be a commercially available transducer able to measure pressures between 0 and $10^6$ Pa. The measurement circuit is shown in FIG. 7. The output of transducer 40 is fed to a mathematic amplifier 197 which may also be commercially available. Its zero-point is set by suitable setting means 196 and is set for atmospheric conditions. Its high calibration point is set by suitable calibration means 195, e.g. equal to a pressure of $4.10^5$ Pa. The output signal of the amplifier 197 is supplied to a further amplifier 199 which amplifies and buffers the output signal and delivers an output signal out-$P_{NO}$ on output 200.

The analog output signal 198 of amplifier 197 is also supplied to a display 201, which may be of a commercially available type, and which converts the signal from analog to digital and shows a numeric value.

As shown in FIG. 7, the pressure transducer 40 is supplied with a reference voltage $Vref_3$ through an input 194.

An electronic system for measuring the pressure P3 in the measuring chamber 88, the NO gas flow, the NO2 gas flow, the O2 gas flow and the pressure P2 present in the outlet manifold of the pneumatic TGI module 10p is also shown in FIG. 8.

The pressure P2 in the outlet line 69 in the TGI module 10p (FIG. 3) is determined by transducer 68, which may be of a commercially available type and is able to detect pressures between 0 and $10^5$ Pa. The output signal of transducer 68 is fed to a mathematic amplifier 205, which may also be of a commercially available type. Its zero-point is set by suitable setting means 204 for atmospheric conditions and its high calibration point is set by suitable calibration means 203, preferably, to a value of $10^4$ Pa. The amplifier 205 provides an output signal 206 to a further amplifier 207 which amplifies and buffers signal 206 and delivers an output signal out-$P_{TGI}$ on an output 208.

Output signal 206 is also fed to an alarm circuitry 210. Alarm circuitry 210 is connected to low level setting means 212 and high setting means 211 which determine the high and low level alarms, respectively. Whenever signal 206 exceeds the high level the alarm circuitry 210 generates a high alarm level signal on a line 134 which is indicated on indicator means 134a. Whenever the signal 206 is below the low level a corresponding alarm signal P2-A is present on a low level signal line 135 which is indicated on an indicator 135a. Of course, the indicators 134a and 135a may be of different colours. The indicators 134a, 135a may be substituted by audible alarms generating different sounds. Alarm lines 134 and 135 are routed to the central alarm circuitry 242 (FIG. 9).

The circuitry is also provided with a display 219 which may be connected either to signal 206 or a high alarm setting line 217 or a low level alarm setting line 218, these latter two alarm setting lines 217, 218 being outputs of the alarm circuitry 210, by means of a switch 209. The switch 209 may be a free-position spring-loaded switch which is manually operable. Thus, display 219 is able to display either the value of the output signal 206 of amplifier 205, or the upper or lower level of the alarm settings.

Pressure transducer 68 is supplied with a reference voltage $Vref_3$ through an input 202.

A timer 213 is provided to supply an apnea time period signal 215 to the alarm circuitry 210, thus, preventing active alarm signals during a period of normal stand still in breathing of a patient. The apnea time period may be set by suitable setting means 214 connected to the timer 213.

The pressure P3 is measured by transducer 91, which may be of a commercially available type able to determine pressures between 0 and $10^5$ Pa. The output of the transducer 93 is fed to a mathematic amplifier 150. The pressure transducer 91 is supplied with a reference voltage $Vref_3$ through an input 149.

The zero-point of mathematic amplifier 150 may be set by suitable setting means 148 for atmospheric conditions and its high calibration point may be set by suitable calibration means 147 to a value of $6.10^3$ Pa. For calibration procedures the amplifier 150 provides an output signal MP3 on output 151. The calibrated output is, e.g., 1 mV/Pa. Through an input 127 the amplifier 150 receives a timing signal from the timer 213. The input signal on input 127 establishes an average output signal MP3 on output 151.

The NO gas flow is measured by NO sensor 26 which is supplied with a reference voltage $Vref_1$ on an input 152.

Sensor 26 provides a low level output signal which is sent to a sensitive, stable mathematic amplifier 155. The zero-point of amplifier 155 is set with suitable setting means 154 whereas the high setting point is set by suitable calibration means 153. The zero-point is set on ambient gas whereas the high setting point is set to a calibrated gas mixture. Pressure signal MP3 is also fed to an input of the amplifier 155. Moreover, the amplifier 155 receives an input signal 183 from an O2 measurement circuit. Besides, the output of amplifier 155 depends on the specific pressure dependency of the cell in use. NO sensors are commercially available in several types. If very accurate measurements are made, the NO sensor may be influenced by the other sensors 27 and 91, for which correction is, then, required. The influence of the NO gas must be slight.

Amplifier 155 provides an output signal 156 to a further amplifier 157 which amplifies and buffers signal 156 and delivers an output signal out-NO on an output 158.

Output signal 156 is also fed to an alarm circuitry 160. The alarm circuitry 160 has a lower level setting by means of suitable setting means 162 and a higher level setting by means of suitable setting means 161. The alarm circuitry 160 provides an output signal NO-A. Whenever alarm output signal NO-A exceeds a predetermined level a corresponding alarm signal is present on a line 128 which is indicated by an indicator 128a. Whenever the alarm output signal NO-A is below a predetermined low level a low level alarm signal is present on a line 129 which is indicated by an indicator 129a. Preferably, the indicators 128a, 129a are of a different colour. Alternatively, alarms of different sounds may be used.

The alarm circuitry 160 is also provided with two outputs 163, 164. On the output 163 a high level alarm setting signal is present whereas on the output 164 a low level alarm setting signal is present. A display 165 is provided the input of which may be connected to either the output signal 156 of the amplifier 155, the output 163 or the output 164 of the alarm circuitry 160 for indicating the respective signals on these outputs. Display 165 converts any analog input signal to a digital signal and shows it as a numeric value. Switch 159 may be a three-position spring loaded switch that is manually operable. Alarm line NO-A is routed to the central alarm circuitry 242 (FIG. 9).

The NO2 gas flow is measured by NO2 sensor 28 which is supplied with a reference voltage $Vref_1$ through an input 166. The output of the sensor 128 is a low level signal which is fed to a sensitive, stable mathematic amplifier 169. The zero-point setting of the amplifier 169 is set by suitable setting means 168 whereas the high setting is set by suitable calibration means 167. The zero-setting is on ambient gas whereas the high setting is on a calibrated gas mixture. The amplifier 169 is also supplied with the pressure signal MP3 output signal 156 of the NO measurement circuit and output signal 184 of the O2 measurement circuit. Moreover the output of amplifier 169 depends on the specific pressure dependency of the NO2 sensor in use. NO2 sensors are commercially available in several types. If very accurate NO2 measurements are made, NO2 sensor 28 may be influenced by sensors 26, 27, 91 for which correction is required.

The output signal 170 of amplifier 169 is fed to an amplifier 171 which amplifies and buffers signal 170 and delivers an output signal out-NO2 on an output 172.

Output signal 170 is also fed to an alarm circuitry 174 which is provided with suitable setting means 175 and 176 for a high alarm level setting and a low level alarm setting, respectively. The alarm circuitry 174 is provided with an output for supplying an alarm output signal NO2-A. Whenever the alarm signal NO2-A exceeds a predetermined value a corresponding high level signal is present on a line 130 which is indicated by an indicator 130a. Whenever the alarm signal NO2-A is below a predetermined low level an alarm signal is present on line 131 which is indicated by an indicator 131a. Of course, the indicators 130a, 131a may be of different colours. Alternatively, alarms of different sounds may be used.

The alarm circuitry 174 is provided with two further outputs 177 and 178 for providing a high level alarm setting signal and a low level alarm setting signal. A display 179 is provided the input of which may be connected to either output signal 170 of the amplifier 169 or to any of the outputs 177 or 178 of the alarm circuitry 174. The display 179 converts any analog input signal to a digital signal and displays a numeric value. Switch 173 may be a three-position spring loaded switch that may e.g. be used to monitor the settings of the high level alarm setting signal and low level alarm setting signal on output 177 and 178 while they are being set by means of the setting means 175 and 176, respectively. Alarm line $NO_2$-A is routed to the central alarm circuitry 242 (FIG. 9).

The O2 gas flow is measured by O2 sensor 27 which is provided with a reference voltage $Vref_2$ through an input 180. The output of the sensor is a low level signal which is fed to a sensitive, stable mathematic amplifier 183. The amplifier 183 has a two-point calibration, a zero on ambient gas by means of suitable setting means 182 and a high setting by means of suitable setting means 181 on a calibrated gas mixture. The amplifier 183 provides an output signal 184 which is fed back to the NO measurement circuit and the NO2 flow measurement circuit. Output signal 184 is also fed to an amplifier 185 which amplifies and buffers signal 184 and delivers an output signal out-O2 on an output 186. The amplifier 183 also receives pressure signal MP3 as an input signal. Moreover, the output signal 184 of the amplifier 183 depends on the O2 sensor in use. O2 sensors are commercially available in several types. If very accurate O2 measurements are made, O2 sensor 27 may be influenced by sensors 26, 28, 91 for which correction is required.

Output signal 184 of amplifier 183 is also fed to an alarm circuitry 188 which has a lower alarm setting and a higher alarm setting by means of suitable setting means 190 and 189, respectively. The alarm circuitry 188 is provided with an output to provide an alarm output signal O2-A. Whenever the alarm output signal O2-A exceeds a predetermined high level a corresponding high level alarm signal is present on line 132 which is indicated by a suitable indicator 132a. Whenever output alarm signal O2-A is below a predetermined low level a corresponding low level alarm signal is present on line 133 which is indicated by an indicator 133a. Of course, indicators 132a and 133a may be of different colours. Alternatively, alarms of different sounds may be provided.

The alarm circuitry 188 is provided with two further outputs 191 and 192 for providing a high level alarm setting signal and a low level alarm setting signal as set by the setting means 189 and 190, respectively.

The circuitry also comprises a display 193 the input of which may be connected to output signal 184 of the amplifier 183, or any of the output signals 191, 192 of the alarm circuitry 188 through a three-position switch 187. The three-position switch 187 may be a spring loaded switch.

The display 193 converts any analog input signal to a digital signal and shows a numeric value. Thus, the display 193 is able to show a numeric value of the measured O2 gas flow or any of the high or low level alarm settings as set by setting means 189 and 190. The $O_2$-A signal is routed to the central alarm circuitry 242 (FIG. 9).

The low settings of the O2, NO and NO2 circuitries should be calibrated for ambient conditions, as regards pressure, temperature, 21% oxygen content and zero NO and NO2 content.

The high settings of the NO and NO2 circuitries should be calibrated for a certified gas mixture of NO in the range of 60 to 80 ppm and NO2 in the range of 6 to 8 ppm in N2.

The high setting of the O2 circuitry should be calibrated for a certified gas mixture of 100% O2 and zero NO and NO2 content. The certified calibration gas mixture is vented into a tube from which the measuring system takes its necessary sample.

Now FIG. 9 will be described which shows an example of an energy supply circuitry for providing several reference voltages, an input voltage for heating element 84 (see FIG. 4) and an alarm circuitry 242 (FIG. 9).

The power supply shown in FIG. 9 comprises three terminals 100a, 100b and 100c, terminal 100b being grounded to ground 101. Reference numbers 103, 104 refer to fuses in the phase and the neutral line. Reference number 105 refers to a commercially available power convertor that converts a mains voltage of 100–240 V AC to 24 V DC. The mains voltage is also connected to the measuring sample pump 94 through an on/off switch 106. Between the switch 106 and the measuring sample pump 94 (also shown in FIG. 4) a further switch is provided which is electro-magnetically driven by driver 146 which is controlled by the level electronics 80 (see FIG. 6). An indicator lamp 107 is connected to the measuring sample pump 94 to light up if the pump 94 is in use.

The power convertor 105 is always connected to the mains and supplies 24 V DC to a line 123 for a cooling ventilator 108, a battery pack 109, a power alarm circuitry 121a, a system alarm circuitry 242 and a switch 111. The battery pack is included in case of mains interrupt and/or patient transport. An indicator lamp 110 will light up if power is on. If operational switch 111 is closed a line 124 is connected to line 123 for providing operational power to voltage regulators 113, 114, 115, 116, 117, and 118 which supply voltages +V1, +V2, $Vref_1$, $Vref_2$, $Vref_3$, and $Vref_4$, respectively. This latter state is indicated by indicator lamp 112

The voltage on line 123 is monitored by an alarm circuitry 121a which provides a low voltage alarm signal V-A on an output line 122 when the voltage drops below a predetermined set level which is set by suitable setting means 121b. The alarm status is indicated by an indicator 121c and routed to the central alarm circuitry 242 (FIG. 9). The alarm settings disappear when the voltage returns to the operational range.

Line 124 is connected to a voltage regulator 120 which provides the input voltage for the heating element 84 (see FIG. 4). The voltage regulator 120 is set by suitable setting means 119. If necessary the voltage regulator 120 may be regulated by means of a closed loop and a temperature sensor within the collected water 85 (not shown). Line 123 is also connected to alarm circuitry 242 which is only schematically shown in the right part of FIG. 9. The alarm circuitry 242 receives alarm input signals from any of the lines 122, 125, 126, 128–139 which are the output alarm lines of the alarm circuitry 121a, the level electronics 80 (FIG. 6), the NO alarm circuitry 160, the NO2 alarm circuitry 174, the O2 alarm circuitry 188, the P2 alarm circuitry 210 (FIG. 8), the T1 alarm circuitry 226 (FIG. 10) and the T2 alarm circuitry 237 (FIG. 11), respectively.

The alarm circuitry 242 is connected to a loud speaker 143 or any other suitable audio means for generating an audio alarm signal and to an indicator 144 to indicate any alarm status. The alarm circuitry 242 also receives an input signal from an alarm suppression circuit 142, the suppression time being set by suitable setting means 141. Suppression of an alarm is started by switching a switch 140 connected to alarm suppression circuit 142. The alarm suppression may, e.g., last 3 minutes as set by setting means 141.

The alarm circuitry 242 may be provided with inputs for receiving alarm signals from amplifiers 293, 297, 301, 305 (FIG. 5a), 309, 313, 317, 321, 325, 329, 333, 337 (FIG. 5b).

Figure 10:
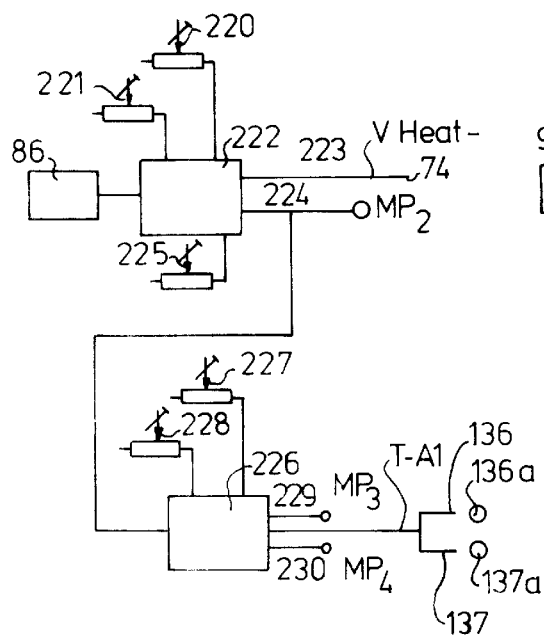
FIG. 10 shows a block diagram of a cooling circuit.

FIG. 10 shows an electrical circuitry for supplying a voltage to the Peltier element 74 to maintain a dewpoint of 8° C. in the water separator 73 to create the dry conditions ideal for measuring the NO, NO2 and O2 concentration in the measuring chamber 88. The actual temperature within the water separator 73 is measured by a temperature sensor 86 which may be a commercially available Pt 100 thermistor. The output signal of the temperature sensor 86 is amplified by an amplifier 222, the zero-point setting of which is set by suitable setting means 221 and the high setting point of which is set by suitable calibration means 220. The zero setting point is calibrated at a low ambient temperature while the high setting point is calibrated at about 40° C. Amplifier 222 compares the output signal of temperature sensor 86 with a predetermined desired temperature which is set by setting means 225. An output voltage VHeat-for the Peltier element 74 is supplied through an output 223. The voltage available on output 223 cools the water separator 73. For calibration procedures the same output value is also available on a further line 224, as a signal MP2. The value of the signal MP2 is also used to check the settings of alarm levels in an alarm circuitry 226. Alarm circuitry 226 has a low setting and a high setting which are set by suitable setting means 228 and 227, respectively. Alarm circuitry 226 provides an alarm output signal T-A1. If the alarm output signal T-A1 exceeds a predetermined level an alarm signal is present on a line 136 which is indicated by an indicator 136a. If the alarm output signal T-A1 is below a predetermined level an alarm signal is present on line 137 which is indicated by indicator 137a. Alarm circuitry 226 is also provided with two further outputs 229, 230 for providing signals MP3 and MP4, respectively, which correspond to the set high level alarm setting 227 and low level alarm setting 228, respectively. The alarms are routed to the central alarm unit.

FIG. 11 shows a voltage regulator for supplying a voltage VHeat+2 to the heating element 89 in the measuring chamber 88 (FIG. 4). Heating element 89 is heated to maintain a constant temperature of about 37° C. in measuring chamber 88 in order to create BTPD conditions. The actual temperature in the measuring chamber 88 is measured by a temperature sensor 92 which may be a commercially available Pt 100 thermistor. The output signal of the temperature sensor 92 is amplified in amplifier 233 which compares the output value of the sensor 92 with a desired temperature which is set by setting means 236. The amplifier 233 is calibrated at a low ambient temperature by setting means 232 and at a high setting point by calibrating means 231. The high setting point is calibrated at about 40° C. Amplifier 233 provides output voltage VHeat+2 on an output 234 for the heating element 89. For calibration procedures the output value is also available on an output 235, as a signal MP5. The value of signal MP5 is also fed to an alarm circuitry 237. Alarm circuitry 237 has a low setting point and a high setting point determined by setting means 239 and 238, respec-tively. Alarm circuitry 237 provides an alarm output signal T-A2. If alarm output signal T-A2 exceeds a predetermined level an alarm signal is present on line 138 which is indicated by indicator 138a. If alarm output signal T-A2 is below a predetermined level an alarm signal is present on line 139 which is indicated by indicator 139a. Alarm circuitry 237 is also provided with two further outputs 240 and 241 for providing output signals MP6 and MP7, respectively, which correspond to the high level alarm setting 238 and the low level alarm setting 239, respectively. These outputs 240 and 241 can, for instance, be used to display the setting points of the alarm circuitry 237 during setting. The alarms are connected to the central alarm unit 242 (FIG. 9).

The measurement circuits for measuring pressure P1 (FIG. 7), pressure P2, NO, NO2 and O2 contents (FIG. 8) are providing visual indications on respective displays 201, 219, 165, 179, and 193 which indications are used by hospital operators to manually adjust according to proper control signals F, Ti and Te supplied by ventilator 21. However, any of the respective output signals out $P_{NO}$, out $P_{TGI}$, out NO, out NO2, and out O2 may be transmitted to suitable electronic feed back circuits (not shown) connected to the ventilator 21 for automatically adjusting according to the control signals F, Ti and Te.

It will be evident to any person skilled in the art that the electronic circuits shown and described can be substituted by either a general purpose computer loaded with suitable software or by suitably programmed dedicated processors, e.g. implemented as single chip elements.

In the description above, a ventilatory system has been described which belongs to the category of "cyclic ventilatory systems with expiration flow". These systems are nowadays applied in highly sophisticated ventilatory machines. The expiration flow in these types of ventilatory systems is used to monitor the patients as accurate as possible. Since in hospitals a trend has started to treat patients with as little anaesthetics as possible synchronisation between patients and machines like ventilatory machines will be needed to an increasing extent. Synchronisation is, preferably, controlled by using the inspiration timing signal Ti, the expiration timing signal Te and the flow signal F, as explained above. Alternatively, only the flow signal F could be used for controlling NO (or any other gas) addition since the flow signal F comprises also all relevant timing data regarding inspiration and expiration phases. In the latter case, means will have to be provided to deduce these data from the flow signal F. The dosage NO applied to a patient is to be optimised in dependence on the expiration phase.

Apart from cyclic ventilatory systems with expiration flow, there are three alternative ventilatory systems in which NO units as described can be applied. The first of these alternatives is the manual ventilatory system shown in FIG. 1b. The two other alternative systems are "continuous flow ventilatory systems" and "cyclic ventilatory systems", which are not shown in the figures and, since they are known to persons skilled in the art, will only be briefly described below.

"Continuous flow ventilatory systems" are mainly used for ventilating children. Inspiration is achieved by closing, during inspiration phases, an output valve to a predetermined amount. The patient expires through a pre-set minimum valve. NO is added continuously during the inspiration phase and the NO concentration is measured by taking samples close to the patient. It is preferred to exhaust both expired gases and sampled gas portions. Here, the NO unit is used for supplying a continuous flow NO to the fresh air flow to be inspired by the patient. Like in manual ventilatory systems, the number of active valves 50–57 are manually controlled. The concentration NO added is regulated by pressure regulators 33 and 38 (FIG. 2). Instead of manually controlling valves 50–57, flow signal F, if available, can be used. As a further alternative, the inspiration timing signal Ti can be used, however, then during expiration phases NO free gas portions may arise. Even a combination of the flow signal and the inspiration timing signal could be used.

In "cyclic ventilatory systems" there is a gas flow to the patient during inspiration phases, which is interrupted during expiration phases. These systems are widely used. NO is added to the patient during inspiration phases. Gas samples for an NO concentration measurement system are taken close to the patient. Again, the required concentration can be set by adjusting manually valves 50–57 and pressure regulators 33, 38. However, this is not preferred since, then, at the beginning of inspiration phases a higher dosage will be applied than at the end. Synchronised NO addition is preferred. Synchronisation is achieved by using the time signals available from the vantilator 21. The pressure and the number of valves 50–57 that may either be closed or opened by the system are set manually. The inspiration timing signal, if available, may control the synchronisation and the flow signal, if available, may control opening and closing of the valves. Alternatively, only the flow signal can be used to control both the synchronisation and the opening and closing of the valves. Again, exhausting both the expired gases and the gas samples for the measurement system is preferred.

It is observed that the system according to the invention, as described above, may be applied in other systems, e.g. in a system for direct NO administration in an arterial blood-vessel towards an organ which has an obstruction in blood-flow caused by vaso-constriction. For that purpose, NO has to be mixed in a physically non-remaining gas such as $CO_2$. Moreover, it may be applied in a system which uses an artificial lung, either alone or combined with another therapy like hemofiltration. Then, NO is added by means of an NO module, as described, in the oxygen inlet of the artificial lung.

What is claimed is:

1. A ventilatory system for ventilating a patient, comprising:

a ventilator provided with at least one first inlet for supplying a predetermined first gas mixture to said ventilator and at least one outlet for supplying a controlled amount of said predetermined first gas mixture to said patient during inspiration intervals; and a gas administration module connected either downstream or upstream from said ventilator and arranged for administering a predetermined amount of an additional gas to said patient, said gas administration module being provided with a predetermined number of valve units which are connected in parallel and can each be independently switched between a closed state and an open state for supplying a predetermined amount of said additional gas to said patient, each of the valve units being provided with a series connection of a throttle valve with a throttle valve inlet and outlet and a controlled valve with a controlled valve inlet and outlet, said controlled valve being switchable between an open and a closed state with a predetermined frequency, said throttle valve outlet being connected to said controlled valve inlet such that there is a passage with a volume V between said throttle valve and said controlled valve that is selected to be so small that the pressure within the passage is returned to the pressure at the throttle valve inlet at any time the controlled valve opens.

2. A ventilatory system according to claim 1 where any of said throttle valves is a needle valve provided with an outlet element having an orifice and an adjustable stem assembly for at least partly closing off said orifice.

3. A ventilatory system according to claim 1 where said volume V is less than 10 $mm^3$.

4. A ventilatory system according to claim 3 where said volume V is less than 3 $mm^3$.

5. A ventilatory system according to claim 1 where said frequency corresponds to switching said controlled valve at least 5 times every inspiration interval.

6. A ventilatory system according to claim 1 where said valve units in their open states allow flow rates rising from a predetermined low value to a predetermined high value in accordance with a predetermined mathematical relationship.

7. A ventilatory system according to claim 6 where said mathematical relation corresponds to a binary flow bench.

8. A ventilatory system according to claim 1 where said additional gas is NO gas.

9. A ventilatory system according to claim 6 where said additional gas is NO gas and said flow rates are selected to allow administration of additional NO gas to said predetermined first gas mixture in a range of 0.05 ppm to 100 ppm.

10. A ventilatory system according to claim 1 where any of said controlled valves is an electromagnetic valve.

11. A ventilatory system according to claim 1 where said ventilator is provided with an electrical ventilator output for providing control signals and said gas administration module is provided with an electrical input coupled to said electrical ventilator output for receiving said control signals in order to automatically control said supplying said predetermined amount of said additional gas to said patient.

12. A ventilatory system according to claim 11 where said electrical input is provided with at least a first input for receiving a flow control signal for controlling the amount of administered additional gas and a second input for receiving an inspiration control signal for controlling that the additional gas is administered at least during inspiration intervals of said patient.

13. A ventilatory system according to claim 12 where said gas administration module is provided with an electronic gas administration module which has a first amplifier connected to said first input and having a gain switchable between a high and a low value by means of a gain switch, the high and low values of said gain corresponding to normal and high flow applications, respectively.

14. A ventilatory system according to claim 13 where said electronic gas administration module is provided with a divider having a divider input connected to said second input for receiving said inspiration control signal and having a divider output for providing a divider output signal which corresponds to said inspiration control signal divided by a selectable dividing number, said divider output being connected to drivers of said valve units for controlling time sections of inspiration intervals during which said additional gas is administered.

15. A ventilatory system according to claim 13 where said electronic gas administration module is provided with a third input for receiving an expiration control signal, a logic unit either connectable to said third input through a further divider or to a predetermined voltage by a second switch which is switched concurrently with said gain switch and which logic unit, when connected to said third input, is arranged for opening a preselected number of said valve units during expiration intervals and, when connected to said predetermined voltage, is arranged for closing at least one of said preselected number of said valve units during expiration intervals.

16. A ventilatory system according to claim 1 further comprising a TGI module provided with a pneumatic TGI module and an electronic TGI module, said pneumatic TGI module having a TGI inlet for receiving a predetermined second gas mixture and a TGI outlet for providing a predetermined amount of said second gas mixture, at least one TGI valve unit connected between said TGI inlet and said TGI outlet, and a pressure limiting security valve connected downstream from said at least one TGI valve unit, said electronic TGI module having an electrical driving unit connected to said at least one TGI valve unit for controlling opening and closing of said at least one TGI valve unit.

17. A ventilatory system according to claim 16 where said at least one TGI valve unit comprises a first TGI valve connected to the TGI inlet and a second TGI valve connected downstream from said first TGI valve, said electrical driving unit having a first electrical driver connected to said first TGI valve and a second electrical driver connected to said second TGI valve, said electronic TGI module and said first and second electrical drivers being arranged to open said first TGI valve outside inspiration flow intervals and to open said second TGI valve outside inversed inspiration intervals.

18. A ventilatory system according to claim 16 where said first TGI valve means are provided with a first and a second controlled TGI valve in parallel, and said second TGI valve means are provided with a third and a fourth controlled TGI valve in parallel.

19. A ventilatory system according to claim 16 where said TGI inlet is connected to an air supply and an oxygen supply through a series connection of a blender, a needle valve, and a flow meter.

20. A ventilatory system according to claim 16 where said pneumatic TGI module is provided with a pressure sensor to measure the pneumatic TGI module outlet pressure and to transmit a corresponding TGI outlet pressure signal to said electronic TGI module and said electronic TGI module is arranged to close said at least one TGI valve means whenever said TGI outlet pressure is not within a predetermined adjustable range.

21. A ventilatory system according to claim 1 further comprising a measuring system comprising a measuring chamber, at least one gas component measuring sensor within said measuring chamber, a sample port for receiving gas samples, a water separator provided with a water separator inlet connected to said sample port, said water separator having a cooling unit for cooling said water separator to a dewpoint temperature between $0°$ C. and $10°$ C., a first water separator outlet connected to a water discharge for draining separated water, and a second water separator outlet connected to said measuring chamber for providing dried gas samples.

22. A ventilatory system according to claim 21 where said water separator is provided with a predetermined volume of cooling liquid which is cooled by said cooling unit, the water separator being arranged such that, in operation, the gas samples are led through said cooling liquid.

23. A ventilatory system according to claim 22 further provided with a cooling liquid level control unit for controlling the level of said cooling liquid within said water separator.

24. A ventilatory system according to claim 21 where the measuring chamber comprises an NO sensor, an $O_2$ sensor, an $NO_2$ sensor, and a pressure sensor.

25. A ventilatory system according to claim 24 where said sample port is connected downstream from said gas administration module.

* * * * *